(12) United States Patent
Hananel et al.

(10) Patent No.: US 12,383,768 B2
(45) Date of Patent: Aug. 12, 2025

(54) IMAGE GUIDED FOCUSED ULTRASOUND TREATMENT DEVICE AND AIMING APPARATUS

(71) Applicant: FusMobile Inc., Alpharetta, GA (US)

(72) Inventors: Ari Hananel, Alpharetta, GA (US); Ron Aginsky, Haifa (IL); Yoav Medan, Haifa (IL)

(73) Assignee: FUS MOBILE INC., Alpharetta, GA (US)

( * ) Notice: Subject to any disclaimer, the term of this patent is extended or adjusted under 35 U.S.C. 154(b) by 98 days.

(21) Appl. No.: 15/752,116

(22) PCT Filed: Aug. 10, 2016

(86) PCT No.: PCT/US2016/046328
§ 371 (c)(1),
(2) Date: Feb. 12, 2018

(87) PCT Pub. No.: WO2017/027577
PCT Pub. Date: Feb. 16, 2017

(65) Prior Publication Data
US 2018/0236270 A1    Aug. 23, 2018

Related U.S. Application Data

(60) Provisional application No. 62/333,896, filed on May 10, 2016, provisional application No. 62/238,263, (Continued)

(51) Int. Cl.
*A61N 7/02*    (2006.01)
*A61B 18/00*    (2006.01)
(Continued)

(52) U.S. Cl.
CPC .............. *A61N 7/02* (2013.01); *A61B 90/37* (2016.02); *A61B 90/39* (2016.02); *A61N 7/00* (2013.01);
(Continued)

(58) Field of Classification Search
CPC ... A61B 90/37; A61B 90/39; A61B 2090/376; A61B 2090/3762; A61B 2090/3764;
(Continued)

(56) References Cited

U.S. PATENT DOCUMENTS 4,938,217 A  *  7/1990  Lele .................... A61N 7/02
                                                    601/3
5,285,772 A  *  2/1994  Rattner ............. A61B 17/2255
                                                    378/205
(Continued)

FOREIGN PATENT DOCUMENTS

CN    100525722    8/2009
CN    102430211    5/2012
(Continued)

OTHER PUBLICATIONS

International Search Report of Application No. PCT/US16/46328 mailed on Nov. 24, 2016.
(Continued)

*Primary Examiner* — John D Li
(74) *Attorney, Agent, or Firm* — PEARL COHEN ZEDEK LATZER BARATZ LLP

(57) ABSTRACT

Apparatus, methods and kits are provided for X-ray guided focused ultrasound treatment that simplify focused ultrasound treatment. The apparatus comprises an arm, a cradle, a focused ultrasound (FUS) transducer having a central axis that is affixed in to the cradle and configured to transmit an ultrasound therapeutic energy beam to a treatment location within a patient and an imaging workstation connected to an
(Continued)

X-ray imaging unit. The FUS is further connected to a controller to control application of the FUS. The kits are utilizing coupling member (s).

13 Claims, 19 Drawing Sheets

Related U.S. Application Data filed on Oct. 7, 2015, provisional application No. 62/203,114, filed on Aug. 10, 2015.

(51) Int. Cl.
 *A61B 90/00* (2016.01)
 *A61N 7/00* (2006.01)
(52) U.S. Cl.
 CPC ........... *A61B 2018/00577* (2013.01); *A61B 2090/376* (2016.02); *A61B 2090/3762* (2016.02); *A61B 2090/3764* (2016.02); *A61B 2090/3966* (2016.02); *A61B 2090/3983* (2016.02); *A61N 2007/0086* (2013.01); *A61N 2007/0091* (2013.01)
(58) Field of Classification Search
 CPC .... A61B 2090/3966; A61B 2090/3983; A61B 2018/00577; A61N 7/00; A61N 7/02; A61N 2007/0086; A61N 2007/0091
 See application file for complete search history.

(56) References Cited

U.S. PATENT DOCUMENTS

| | | | |
|---|---|---|---|
| 5,350,351 A | 9/1994 | Saffer | |
| 5,388,581 A | 2/1995 | Bauer et al. | |
| 5,488,951 A * | 2/1996 | Bauer | A61B 6/12 |
| | | | 378/162 |
| 7,305,264 B2 | 12/2007 | Larson et al. | |
| 7,553,284 B2 | 6/2009 | Vaitekunas | |
| 8,197,409 B2 | 6/2012 | Foley et al. | |
| 8,512,262 B2 | 8/2013 | Gertner | |
| 8,727,987 B2 | 5/2014 | Chauhan et al. | |
| 8,831,708 B2 | 9/2014 | Paladini et al. | |
| 9,161,735 B2 | 10/2015 | Bradford et al. | |
| 9,579,518 B2 | 2/2017 | Gertner | |
| 10,231,712 B2 | 3/2019 | Ebbini et al. | |
| 2002/0002345 A1 | 1/2002 | Marlinghaus | |
| 2003/0060736 A1* | 3/2003 | Martin | A61N 7/02 |
| | | | 601/2 |
| 2003/0151720 A1* | 8/2003 | Chernyak | A61B 3/14 |
| | | | 351/206 |
| 2005/0054955 A1 | 3/2005 | Lidgren | |
| 2005/0154308 A1 | 7/2005 | Quistgaard et al. | |
| 2007/0237290 A1 | 10/2007 | Mostafavi | |
| 2007/0276297 A1* | 11/2007 | Fadler | A61B 17/2255 |
| | | | 601/2 |
| 2009/0030308 A1 | 1/2009 | Bradford et al. | |
| 2009/0156894 A1 | 6/2009 | Hagelauer | |
| 2010/0081893 A1 | 4/2010 | Jarvik et al. | |
| 2010/0210976 A1 | 8/2010 | Darlington | |
| 2010/0280420 A1 | 11/2010 | Barthe et al. | |
| 2010/0312103 A1* | 12/2010 | Gorek | A61B 6/547 |
| | | | 600/425 |
| 2011/0144544 A1 | 6/2011 | Fan et al. | |
| 2011/0201929 A1 | 8/2011 | Vaezy et al. | |
| 2012/0143100 A1* | 6/2012 | Jeong | A61N 7/02 |
| | | | 601/2 |
| 2012/0238919 A1 | 9/2012 | Gertner | |
| 2013/0131494 A1* | 5/2013 | Salomir | A61B 90/37 |
| | | | 600/411 |
| 2013/0144165 A1 | 6/2013 | Ebbini et al. | |
| 2013/0218024 A1* | 8/2013 | Boctor | A61B 8/4416 |
| | | | 600/476 |
| 2013/0239689 A1* | 9/2013 | Bbond-Thor | G01N 29/262 |
| | | | 73/625 |
| 2014/0018708 A1 | 1/2014 | Dunbar et al. | |
| 2014/0155747 A1* | 6/2014 | Bennett | H04R 31/00 |
| | | | 600/439 |
| 2014/0236051 A1* | 8/2014 | Kim | A61B 8/4483 |
| | | | 601/3 |
| 2014/0276055 A1* | 9/2014 | Barthe | A61B 8/4466 |
| | | | 600/439 |
| 2015/0146955 A1* | 5/2015 | Dong | G06T 11/008 |
| | | | 382/131 |
| 2015/0305823 A1* | 10/2015 | Claus | A61B 34/20 |
| | | | 600/424 |
| 2016/0059044 A1* | 3/2016 | Gertner | A61B 90/37 |
| | | | 601/2 |
| 2017/0143429 A1* | 5/2017 | Richmond | A61B 34/20 |

FOREIGN PATENT DOCUMENTS

| | | |
|---|---|---|
| CN | 102781516 | 11/2012 |
| DE | 4302538 C1 | 4/1994 |
| DE | 102010018857 A1 | 12/2010 |
| EP | 0627206 A2 | 12/1994 |
| EP | 2332614 A1 | 6/2011 |
| FR | 2827149 A1 | 1/2003 |
| JP | H02-114953 | 4/1990 |
| JP | H03-141938 | 6/1991 |
| JP | H05-237131 | 9/1993 |
| JP | H06-233776 | 8/1994 |
| JP | H08-131454 | 5/1996 |
| JP | 2002-502622 | 1/2002 |
| JP | 2005-304909 | 11/2005 |
| JP | 2007-507275 | 3/2007 |
| JP | 2007-525296 | 9/2007 |
| JP | 2008-100055 | 5/2008 |
| JP | 2009-533086 | 9/2009 |
| JP | 2012-005602 | 1/2012 |
| JP | 2012-239791 | 12/2012 |
| JP | 2013-505789 | 2/2013 |
| JP | 2015-521490 | 7/2015 |
| WO | WO/2007140331 | 12/2007 |
| WO | WO 2008/118300 A1 | 10/2008 |
| WO | WO 2010/009141 A1 | 1/2010 |
| WO | WO 2011020104 | 2/2011 |
| WO | WO/2013048912 | 4/2013 |
| WO | WO 2013/128349 | 9/2013 |
| WO | WO 2014/139023 | 9/2014 |
| WO | WO 2014193013 | 12/2014 |

OTHER PUBLICATIONS

International Search Report of PCT Application No. PCT/IL2015/050855 mailed Dec. 10, 2015.
Chinese Office Action of Application No. 2015800580387 mailed on Oct. 15, 2018.
Japanese Office Action of Application No. 2018-507005 mailed on Aug. 11, 2020.
United States Office Action of U.S. Appl. No. 15/506,758 mailed on Dec. 27, 2018.
Japanese Office Action of Application No. 2017-530452 mailed on Jun. 4, 2019.
Office Action of Chinese Application No. 2020111474191 mailed on Mar. 29, 2023.
Office Action for Japan Patent Application No. 2023-026660, mailed on Dec. 12, 2023.
Office Action of JP Application No. 2018-507005 mailed on Jun. 15, 2021.

* cited by examiner

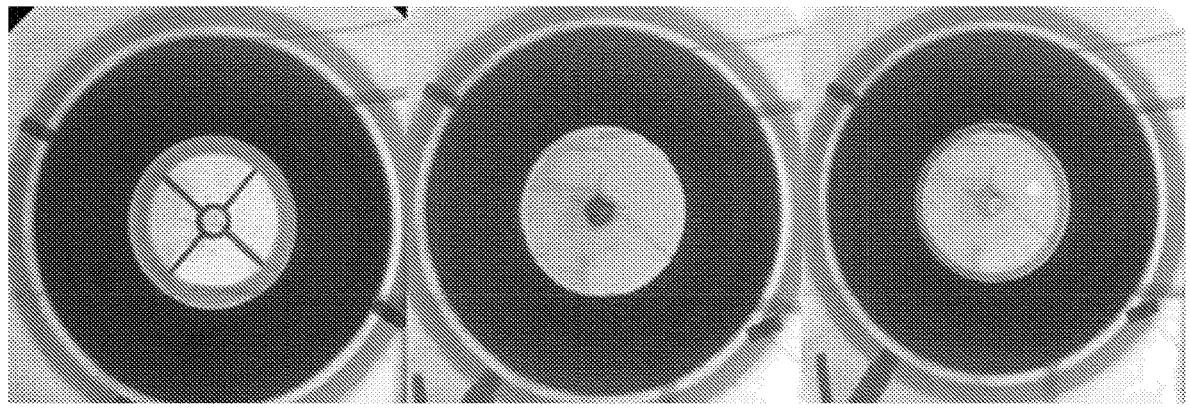
FIGURE 12A   FIGURE 12B   FIGURE 12C
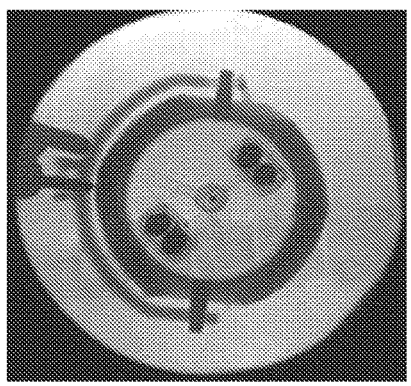   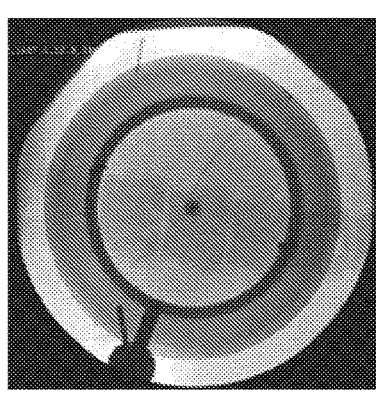
FIGURE 12D   FIGURE 12E

IMAGE GUIDED FOCUSED ULTRASOUND TREATMENT DEVICE AND AIMING APPARATUS

CROSS-REFERENCE TO RELATED APPLICATIONS

This application is a National Phase Application of PCT International Application No. PCT/US16/46328, International Filing Date Aug. 10, 2016, claiming priority of U.S. Patent Applications Nos. 62/203,114, filed Aug. 10, 2015, 62/238,263, filed Oct. 7, 2015, and 62/333,896, filed May 10, 2016, which are hereby incorporated by reference.

BACKGROUND OF THE INVENTION

1. Technical Field

The present invention relates to the field of focused ultrasound (FUS), and more particularly, to the field of X-Ray guided FUS devices.

2. Discussion of Related Art

FIG. 1 is a high level schematic illustration of a prior art radiofrequency (RF) nerve ablation procedure. The RF ablation procedure includes thermal destroying of medial branch nerves that innervate a painful and inflamed joint 70. The RF ablation procedure is performed in a clinic or a hospital setting with the guidance of X-Ray, which is used by the treating physician to guide the tip of a needle 92 to a junction of a transverse articular process 71 and a superior articular process 72 of facet joint 73 of a targeted vertebra, placing the needle along the path of medial nerve branch 91. Needle 92 generates heat at its tip via the RF energy and thermally coagulates the tissue in a small cylindrical shape around its tip, which also contains the medial nerve branch. The prior art ablation procedure is an invasive, uncomfortable and painful procedure that carries risk of infection and bleeding for the patients.

SUMMARY OF THE INVENTION

The following is a simplified summary providing an initial understanding of the invention. The summary does not necessarily identify key elements nor limits the scope of the invention, but merely serves as an introduction to the following description.

An X-Ray guided apparatus for an image guided focused ultrasound treatment, comprises: an articulated arm attached at its base to a procedure platform; a cradle affixed to the distal end of the arm; an aiming apparatus affixed in the cradle; a focused ultrasound (FUS) transducer having a central axis that is affixed in to the cradle and configured to transmit an ultrasonic therapeutic energy beam to a treatment location within a patient, wherein the FUS transducer is connected to a controller to control application of focused ultrasound by the transducer; and an imaging workstation connected to an imaging unit configured to derive imaging data from an X-Ray imaging system.

The apparatus relies on an imaging device such as an X-ray system to assist in aiming the position and orientation of the FUS transducer to guide the focal spot to the treatment location.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 12A-12H are X-ray-images of the FUS transducer including different types of x-ray aims and aiming apparatus, used in the X-Ray guided device according to some embodiments of the invention.

DETAILED DESCRIPTION OF THE INVENTION

Figure 1:
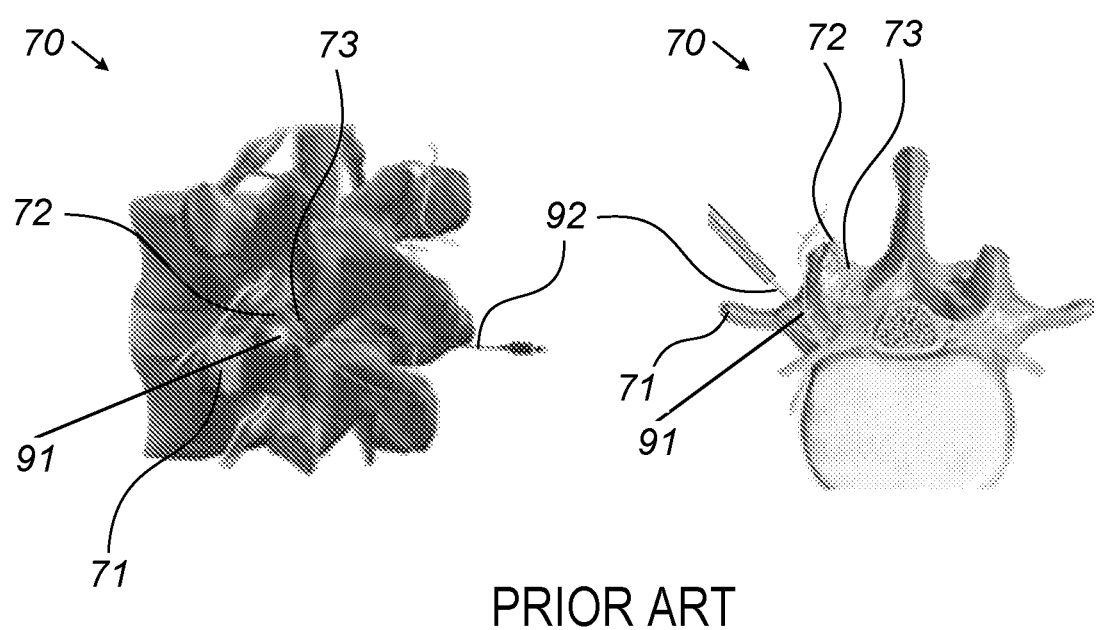
FIG. 1 is a high level schematic illustration of a prior art RF ablation procedure.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

An X-Ray guided apparatus and method for an image guided focused ultrasound (FUS) treatment are provided. The apparatus comprises an articulated arm attached at its base to a procedure platform, a cradle affixed to the distal end of the arm, an aiming apparatus, a FUS transducer and x-ray aim, having a central axis that is affixed in to the cradle and configured to transmit an ultrasonic therapeutic energy beam to a treatment location within a target patient, wherein the FUS transducer is connected to a controller configured to control application of focused ultrasound by the transducer, and an imaging workstation connected to an imaging unit configured to derive imaging data from an X-Ray imaging system. The apparatus may be used in a clinical or hospital setting that is equipped with appropriate imaging device, such as C-Arm, Fluoroscopy or any generic X-ray imaging system. The apparatus may be guided by a pre-operative imaging system, in which the images taken by different imaging system (e.g., CT, an MRI or any other system) may be fused, registered and overlaid with the images generated during the FUS treatment procedure. The apparatus may be used in combination with a C-Arm, an O-Arm, a G-Arm, X-Ray computed tomography (CT) or any other X-Ray device. The apparatus may be compatible with any ultrasound imaging system.

Figure 2:
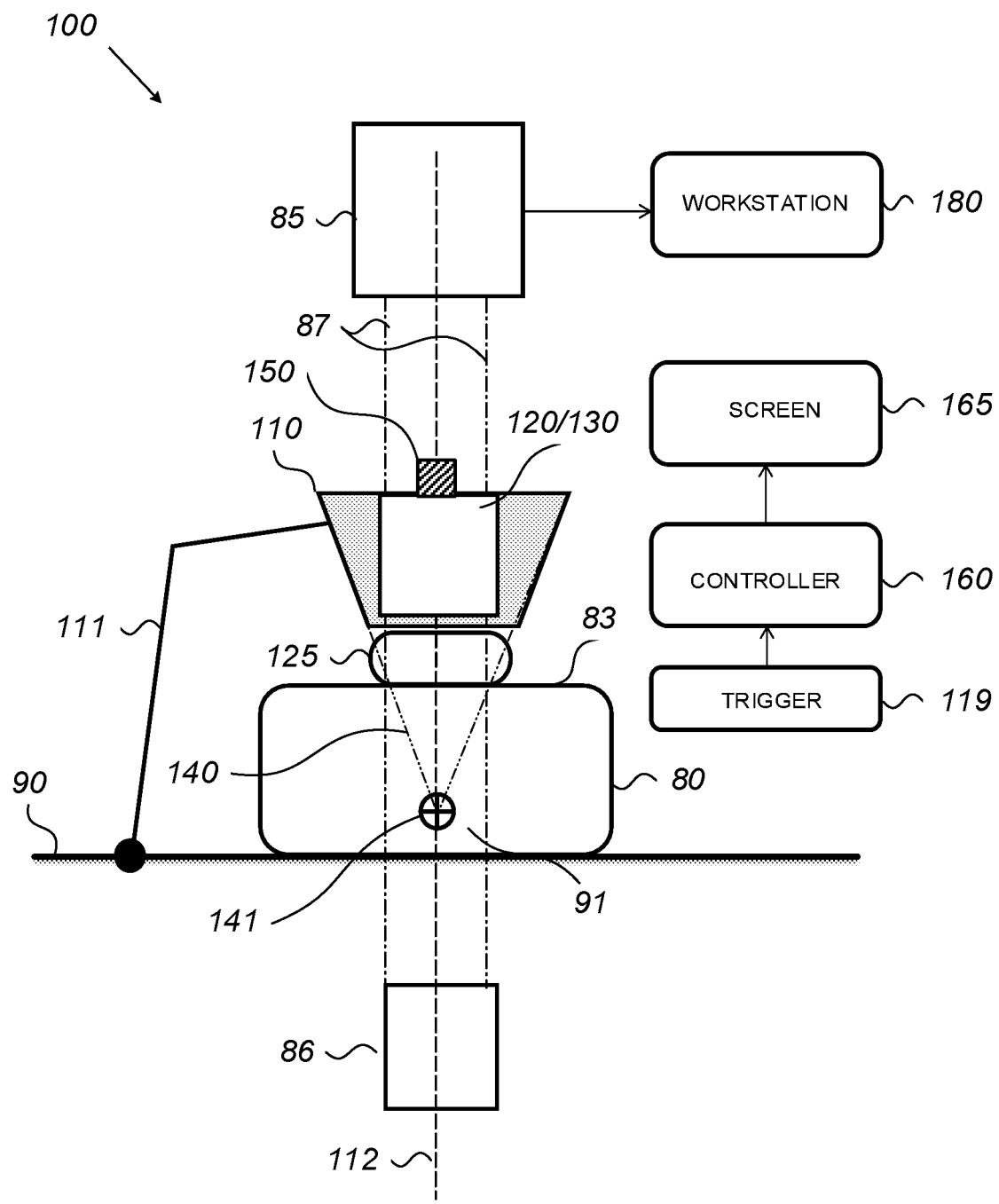
FIG. 2 is a high level schematic illustration of an X-Ray guided focused ultrasound treatment apparatus and its components, according to some embodiments of the invention.

FIG. 2 is a high level schematic illustration of an X-Ray guiding apparatus 100 for an image guided FUS treatment, according to some embodiments of the invention. Apparatus 100 comprises an articulated arm 111 attached at its base to a procedure platform 90. In certain embodiments, procedure platform 90 may comprise at least one of: an operating room table, an imaging table and a dedicated cart, wherein the cart is designed to carry the electronics and other device's accessories and wherein the cart wheels are designed to be locked to avoid the cart's movement. Apparatus 100 may further comprise a cradle 110 attached to the distal end of arm 111. Apparatus 100 may further comprise a coupling accessory 125 configured to acoustically couple transducer surface 120 to a surface 83 of a tissue 80.

Apparatus 100 may further comprise a FUS transducer 120 having a central axis 112 configured to be affixed within cradle 110 and to transmit a FUS energy beam 140 to a treatment location 141 within a patient. Apparatus 100 may further comprise a trigger 119, configured to terminate the delivery of FUS energy 140. Apparatus 100 may further comprise a controller 160 configured to control FUS energy delivery by therapeutic FUS transducer 120 which could be controlled by user interface. Apparatus 100 may further comprise a screen 165. Screen 165 provides the physician technical information, such as, but not limited to, power level chosen, sonication duration, informative maintenance and service messages. Screen 165 may contain the clinical information which in essence the workstation 180 provides, and vice versa workstation 180 may provide the technical information. Apparatus 100 may further comprise an aiming apparatus 130 configured to be affixed within cradle 110. In certain embodiments, cradle 110 may be further configured such that both FUS transducer 120 and aiming apparatus 130 may be affixed within it simultaneously. In certain embodiments, an x-ray aim 150 may be attached to the FUS transducer 120 to enable x-ray guidance. In certain embodiments, cradle 110 may comprise several motion degrees of freedom, such as, but not limited to, anterior-posterior (A-P), superior-interior (S-I), left-right (L-R). In certain embodiments, cradle 110 may be configured to accommodate smoothly the insertion, lock and release of the aiming apparatus and the FUS transducer. In certain embodiments, cradle 110, FUS transducer 120, aiming apparatus 130 and x-ray aim 150 are built as a single unit.

Apparatus 100 may further comprise an X-Ray imaging system, comprising an X-Ray intensifier 85 and an X-Ray source 86, wherein X-Ray intensifier 85 and X-ray source 86 are connected as an X-ray imaging system. In certain embodiments, the X-Ray imaging system may be configured to image a region 91 of tissue 80 that includes a treatment location 141. In certain embodiments, the X-ray imaging may be performed before and during the FUS treatment. In certain embodiments, apparatus 100 may configured to be compatible with at least one of the following X-ray types: a C-arm, an O-arm, a G-arm and any other generic X-Ray type.

Apparatus 100 may further comprise a workstation 180 connected to X-ray intensifier 85 of the X-ray imaging system, wherein workstation 180 configured to derive an imaging data from the X-Ray imaging system. In certain embodiments, controller 160 and screen 165 may be combined within workstation 180.

In certain embodiment, articulated arm 111 may be a mechanical arm or robotic arm that is attached to procedure platform 90. In certain embodiments, articulated arm 111 may comprise several degrees of freedom, such as, but not limited to, anterior-posterior (A-P), superior-interior (S-I), left-right (L-R), and tilt such as, yaw, pitch and roll, to allow the alignment of FUS energy beam 140 to a desired treatment location 141 within the patient. In certain embodiments, articulated arm 111 may be adjusted manually and/or electronically and/or automatically to align it in the predefined orientation and position of cradle 110.

In certain embodiments, apparatus 100 may further comprise a manual or controlled remote maneuvering module configured to remotely control the position and the orientation of articulated arm 111. The maneuvering module may comprise at least one rod connected to articulated arm 111 in a non-limiting manner, and a control unit configured to control the motion of articulated arm 111. The rod may be made of at least one of: a metal, a plastic, a wood and a carbon. The remote control of articulated arm 111 can minimize the exposure of the operating physician to X-radiation. In certain embodiments, the control unit of the maneuvering module may be implemented within controller 160 and/or workstation 180.

In certain embodiments, coupling accessory 125 is designed to mimic the inner shape of FUS transducer 120 to enhance the acoustic coupling quality and provide the desired flexibility to enhance the coupling with patient skin 83. In certain embodiments, coupling accessory 125 may be a balloon or membrane filled with fluid or gel. The balloon or membrane may be affixed to cradle 110 using rubber and/or ring that secure coupling accessory 125 attached to cradle 110 during the procedure.

In certain embodiments, coupling accessory 125 may comprise a gel pad. Gel pad 125 may be designed to mimic the inner shape of FUS transducer 120 including its margins in order to enable angular maneuver flexibility. The margin may provide the operating physician the possibility to manipulate cradle 110 and FUS transducer 120 in different angular positions without adversely affecting the coupling between FUS transducer and gel pad 125. In certain embodiments, gel pad 125 may be designed in a shape that wraps around cradle 110 in order to affix gel pad 125 to cradle 110 during the insertion of FUS transducer 120. Gel pad 125 may also be designed as a convex shape on the side that is attached to patient skin 83. The convex shape may provide the operating physician the possibility to manipulate cradle 110 in different angular position without affecting the coupling between gel pad 125 and patient skin 83. In certain embodiments, coupling accessory 125 may be at least one of: an optically transparent, an acoustically transparent and radiologically transparent. In certain embodiments, coupling accessory 125 may be designed to guide the positioning of the transducer 120 to a predefined angle of penetration of the acoustic beam 140 into the tissue 80.

In certain embodiments, FUS transducer 120 may be configured to deliver FUS energy 140 to different depths according to the position of treatment location 141 using at least one of: different sizes of coupling accessory 125 and/or by tuning phased array transducer elements as electronic steering.

In certain embodiments, FUS transducer 120 may be further configured to project FUS beam energy 140 in a focused manner onto treatment location 141 as the focal spot location, utilizing adjacent bone structures and avoiding damage to adjacent soft tissues. In certain embodiments, FUS transducer 120 may comprise at least one of: a single element or a phased array of elements or two or more annular elements. In certain embodiments, FUS transducer 120 may comprise at least two annular ring elements geometrically focused at a depth within a range 141A in a closed environment of treatment location 141 (see, e.g., FIG. 3B). The annular elements arrangement of FUS transducer 120 allows locating the acoustic focus of FUS beam 140 either proximal or distal to the geometric focal depth by operating each of the at least two annular elements to vibrate at different phase. This allows a single FUS transducer 120 to mimic a series of transducers with the same aperture size but with different geometric focal lengths. This allows the operating physician to adjust, during the procedure, the depth of the acoustic focus of FUS beam 140 to match the depth of treatment location 141, and thereby improve the efficacy of the treatment. In certain embodiments, the different annular elements of the transducer could be driven in slightly different frequency (incoherent mode) which results in continuous change of the relative phase between the elements in order to create elongated acoustic focus. In certain embodiments, at least one of the annular ring elements of FUS transducer 120 may be configured to be turned off in order to avoid from FUS energy beam 140 to hit vertebra bone protrusions or other acoustically absorbing structures in the beam path which should not be exposure to the high intensity acoustic energy. In certain embodiments, central axis 112 of FUS transducer 120 may be tilted relatively to the patient back so that energy beam 140 is transmitted onto treatment location 141 on the vertebra at an angle to the bone structure, thus avoiding a situation where FUS energy 140 may be blocked (e.g., by the vertebra protrusions and lamina). Certain angles may be selected to allow the incidence angle with respect to the bone surface to be smaller than the refraction angle, such that most of FUS energy 140 is absorbed by the bone and not reflected. In certain embodiments, apparatus 100 and projected FUS energy 140 may be used to optimize the incidence angle of the acoustic energy with respect to the bone to maximize absorption of energy by the bone. When beam angle is perpendicular to the bone the absorption of acoustic energy by the bone is maximal.

Figure 3A:
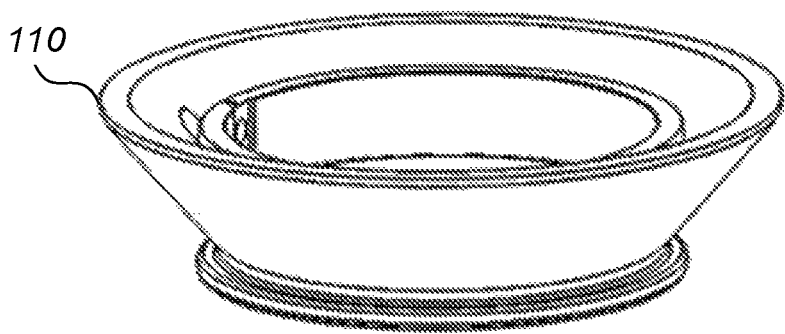
FIGS. 3A-3B are high level schematic illustrations and a lateral X-ray image of a cradle used in the X-Ray guided apparatus, according to some embodiments of the invention.
Figure 3B:
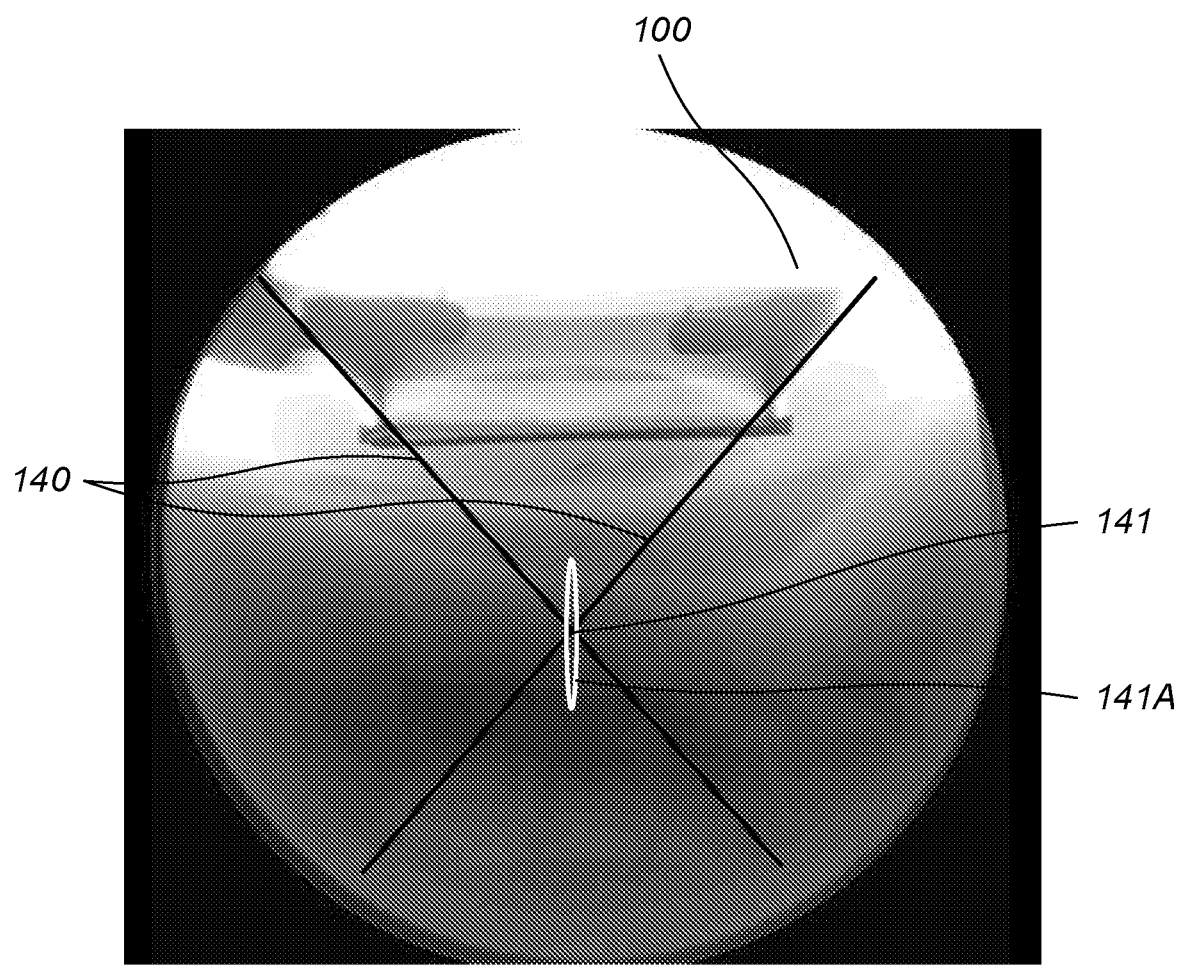

FIG. 3A is a high level schematic illustration of cradle 110. In certain embodiments, cradle 110 is designed to have a geometrical conic shape such that the projections of the cone boundaries are consistent with FUS beams 140 generated by FUS transducer 120. In certain embodiments, the cone shape of cradle 110 is designed such that the lateral projected apex of the cone (e.g., the intersection point of the projections the cone boundaries) corresponds to the focal depth of the FUS energy beams 140. Accordingly, the conic shape of cradle 110 may be used as a marker, visible on the X-Ray image, in order to guide the focusing of FUS energy beam 140 onto treatment location 141, as illustrated in FIG. 3B. FIG. 3B is a high level schematic illustration of a lateral X-ray image of cradle 110, according to some embodiments of the invention. In certain embodiments, workstation 180 may further comprise a software module configured to receive the lateral X-ray image of cradle 110, to send the lateral X-ray image of cradle 110 to screen 165 and, to recognize, using image processing well known in the art, by means of at least one computer processor, the projections of the cone boundaries of cradle 110 and to display these projections on the lateral X-ray image of cradle 110. In the preferred embodiment, the intersection point of the projections the cone boundaries represents the lateral projected apex of the cone, which corresponds to the focal depth of the FUS energy beams 140. Accordingly, the lateral projected apex of the cone may be used to assist the operating physician in navigating FUS energy beam 140 accurately and safely to treatment location 141. The conical geometry of cradle 110 is invariant in wide range of lateral projection images of the lateral views. Accordingly, the cone shape including its apex can be recovered from a range of views. In certain embodiments, cradle 110 may comprise at least one of: a radio opaque material, a radiolucent material coated with radio opaque material and a semi radio opaque material.

In certain embodiments, image guided interventional procedures, in particular frameless stereotactic procedures, involve a stereoscopic optical image sensor that tracks object tagged with special markers to aid registration and navigation of FUS energy beam 140 to a target location 141. Such markers are typically large spheres that can be easily identified within the field of view, or encoded black and white barcode like labels that can also uniquely identify a specific object and track it within the field of view. Spheres are particularly popular because its shape is almost invariant to viewing angle transformations. In 3D imaging modalities like CT or MR, markers are one or two dimensional and are made of a radio opaque or magnetic material to make them visible. For X-Ray (fluoroscopy) guidance, 2D templates with radio opaque markers are typically used for registration with pre-operative 3D imaging data and tracking.

Figure 4A:
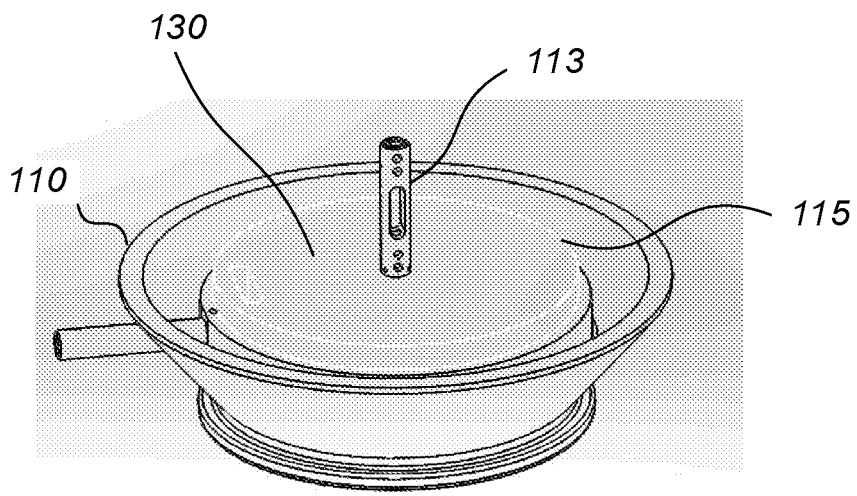
FIG. 4A-4B is high level schematic illustrations and images of an aiming apparatus, (Mock-up with the optical markers and x-ray markers) used in the X-Ray guided apparatus according to some embodiments of the invention.

FIG. 4A is a high level schematic illustration of an aiming apparatus 130 positioned in cradle 110, according to some embodiments of the invention. In certain embodiments, an aiming apparatus 130 may comprise a mockup 115 configured to be positioned in cradle 110. In certain embodiments, mockup 115 may comprise a transparent material (e.g., Perspex) to allow the operating physical to keep patient skin 83 in a field of view. In certain embodiments, mockup 115 may comprise a radiolucent material (e.g., Perspex and Carbon Fibers) to generate clear X-Ray images of target location 141.

In certain embodiments, aiming apparatus 130 may further comprise at least one optical marker holder 113. In certain embodiments, optical marker holder 113 may comprise at least one laser pointer. In certain embodiments, at least one optical marker holder 113 may be aligned to create a straight line along central axis 112 of FUS transducer 120 and cradle 110. In certain embodiments, at least one optical marker holder 113 may be configured to create additional lines to verify the position of cradle 110 and FUS transducer 120 with respect to the normal of the X-ray imaging system field of view 85.

Figure 4B:
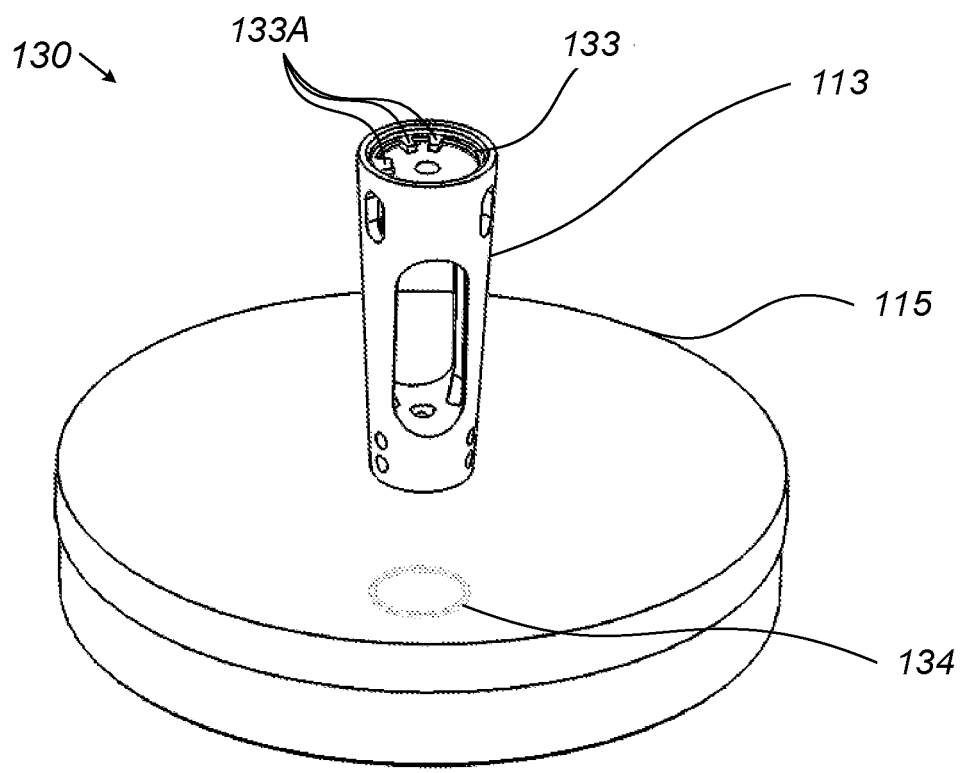

FIG. 4B is a high level schematic illustration of mockup 115 and optical marker holder 113 of aiming apparatus 130, according to some embodiments of the invention. In certain embodiments, aiming apparatus 130 may further comprise at least two x-ray aiming markers 133, 134 positioned on the vertical axis of at least one optical marker holder 113. In certain embodiments, x-ray aiming markers 133, 134 may be rings. At least one x-ray aiming marker 133, 134 may comprise at least one groove 133A. In certain embodiments, at least one of mockup 115 and x-ray aiming markers 133, 134 may be asymmetric, wherein the asymmetry may be visible both optically and on radiologically, enabling the operating physician to correlate both views and conclude on direction and angle of movement as needed to co-align cradle 110 with X-Ray intensifier 85 along central axis 112.

In certain embodiments, at least one of mockup 115 and optical markers holder 113, may have at least one X-Ray fiducial marker to enable the finding of mockup 115 orientation in the X-ray images. In certain embodiments, optical markers holder 113 may have individual on and off switches, affixed or placed adjacent to mockup 115.

Figure 5A:
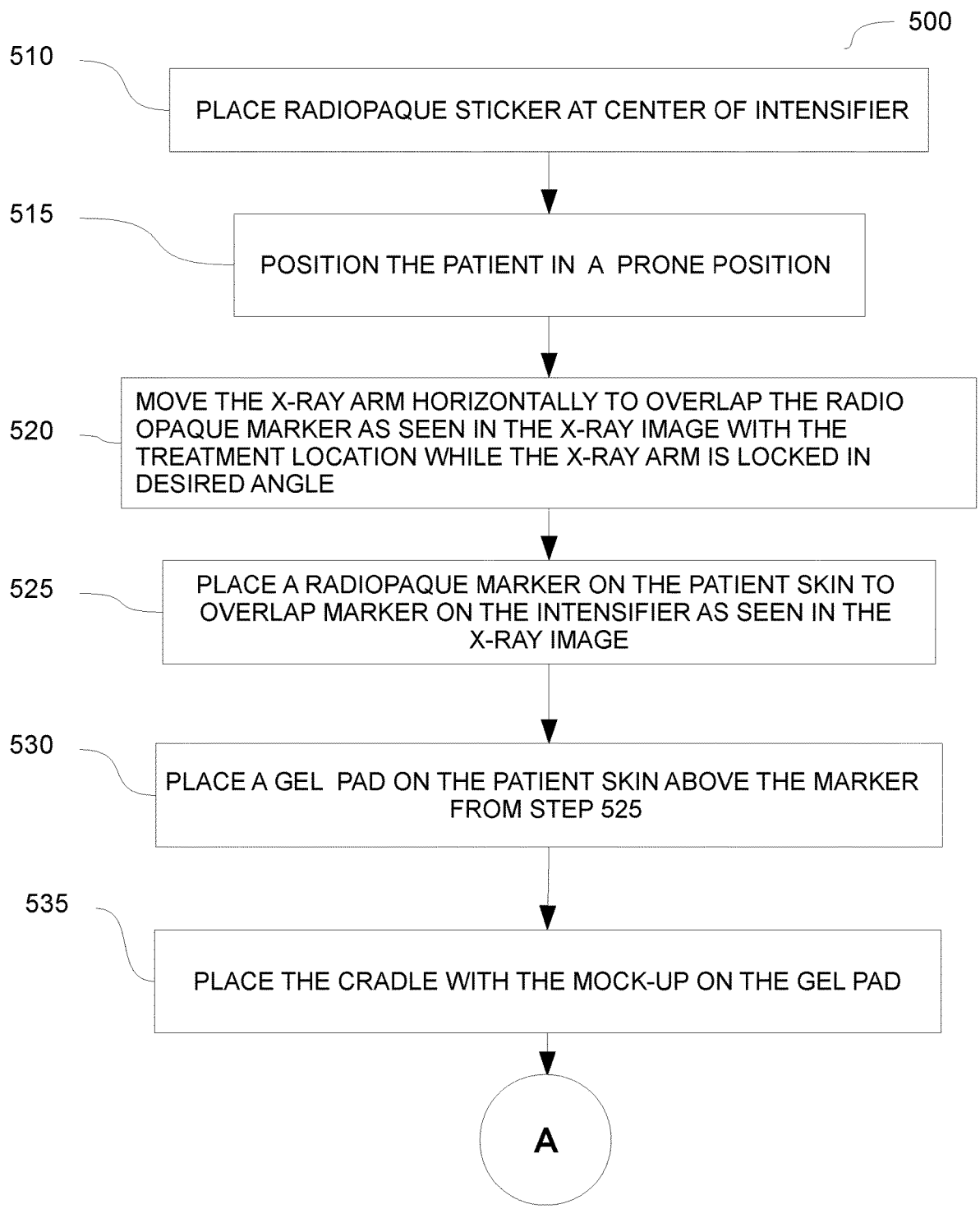
FIGS. 5A-5B is a high level flowchart illustrating a method, according to some embodiments of the invention.
Figure 5B:
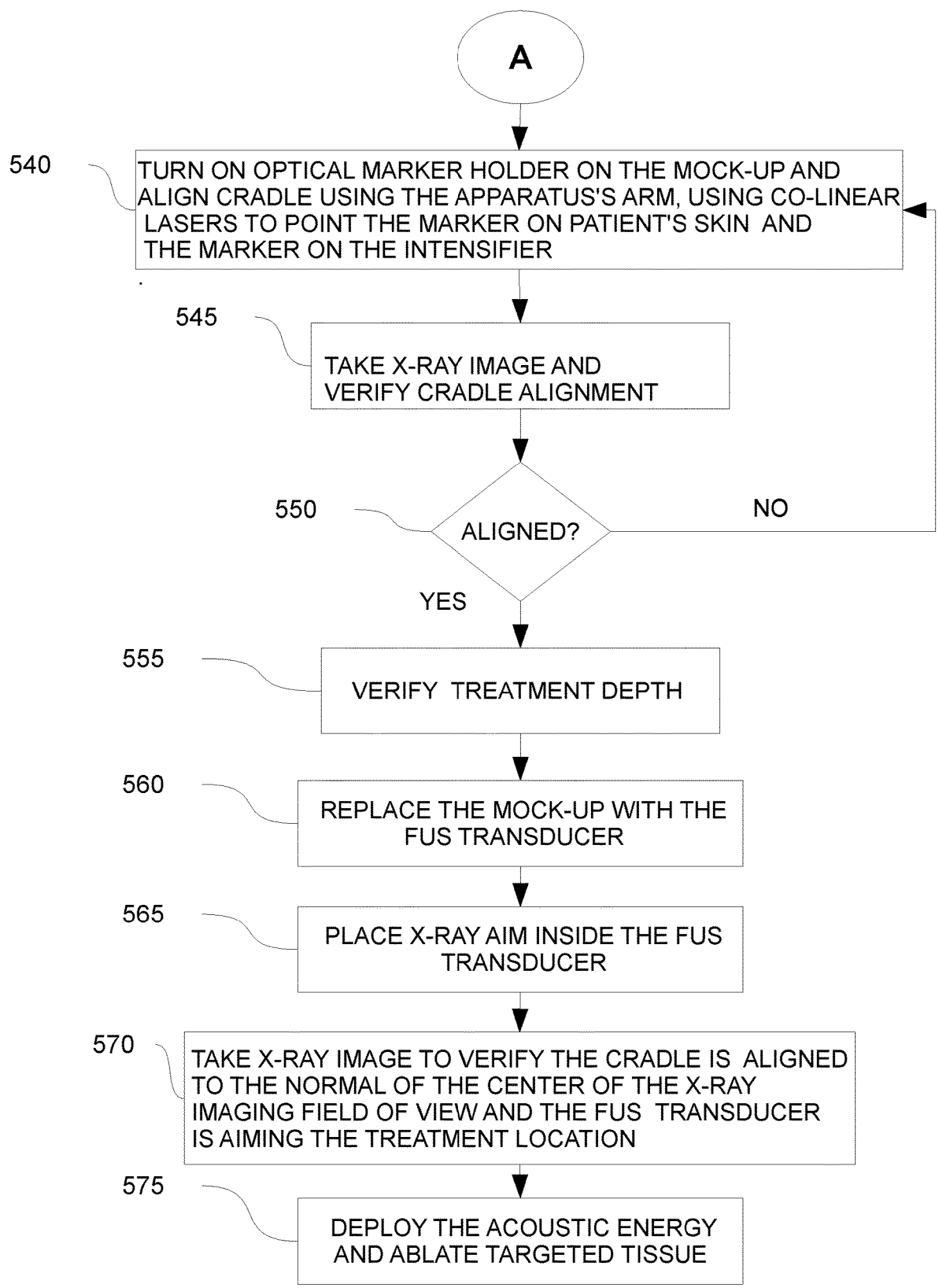

FIGS. 5A-5B is a high level flowchart illustrating a method, according to some embodiments of the invention. At step 510, at least one radio opaque marker is placed at center of X-ray intensifier 85 (see, e.g., 70A in FIG. 6A). At step 515, the patient is positioned in a prone position at procedure platform 90. After the patient is positioned on the table, the relative height of the table and C-Arm is adjusted so both the patient spine and the cradle can be seen within the X-Ray field of view. Once the height is set, it will remain locked throughout the procedure. This adjustment is done via lateral X-Ray image and manipulation of the table height and C-Arm height.

Figure 6A:
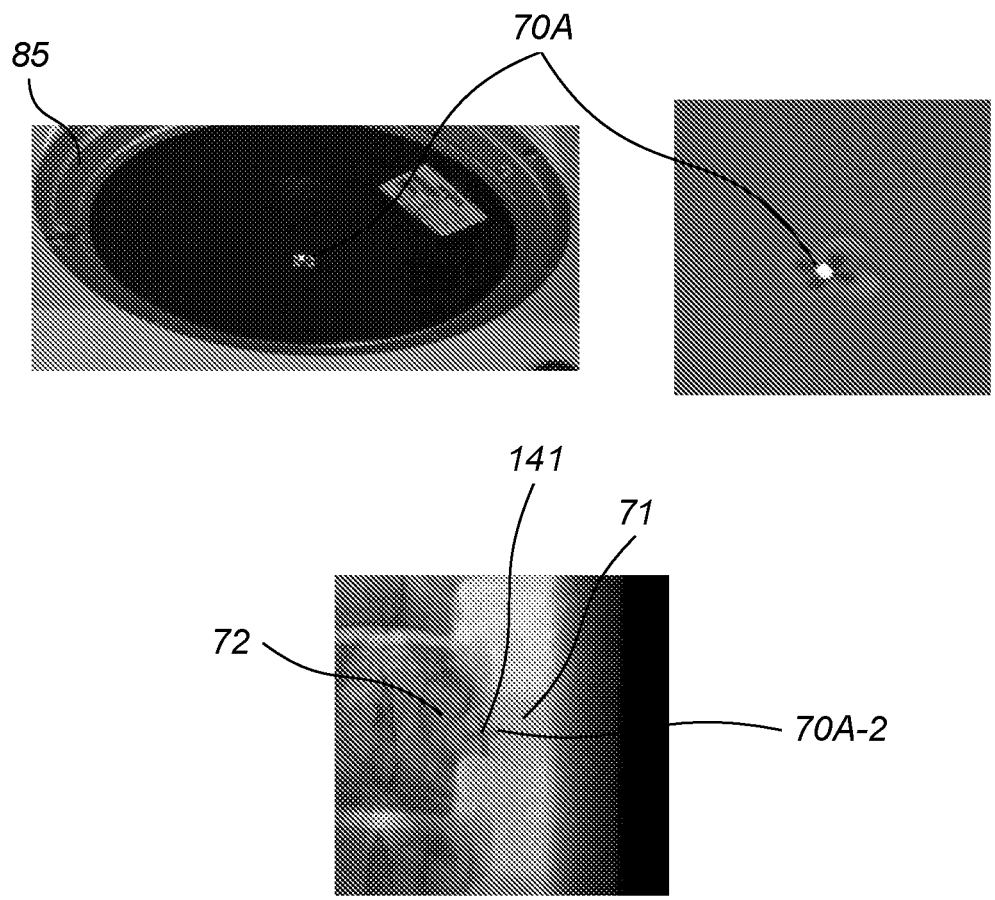
FIGS. 6A-6C is an example of the treatment application, according to some embodiments of the invention used in the X-Ray guided apparatus.
Figure 6B:
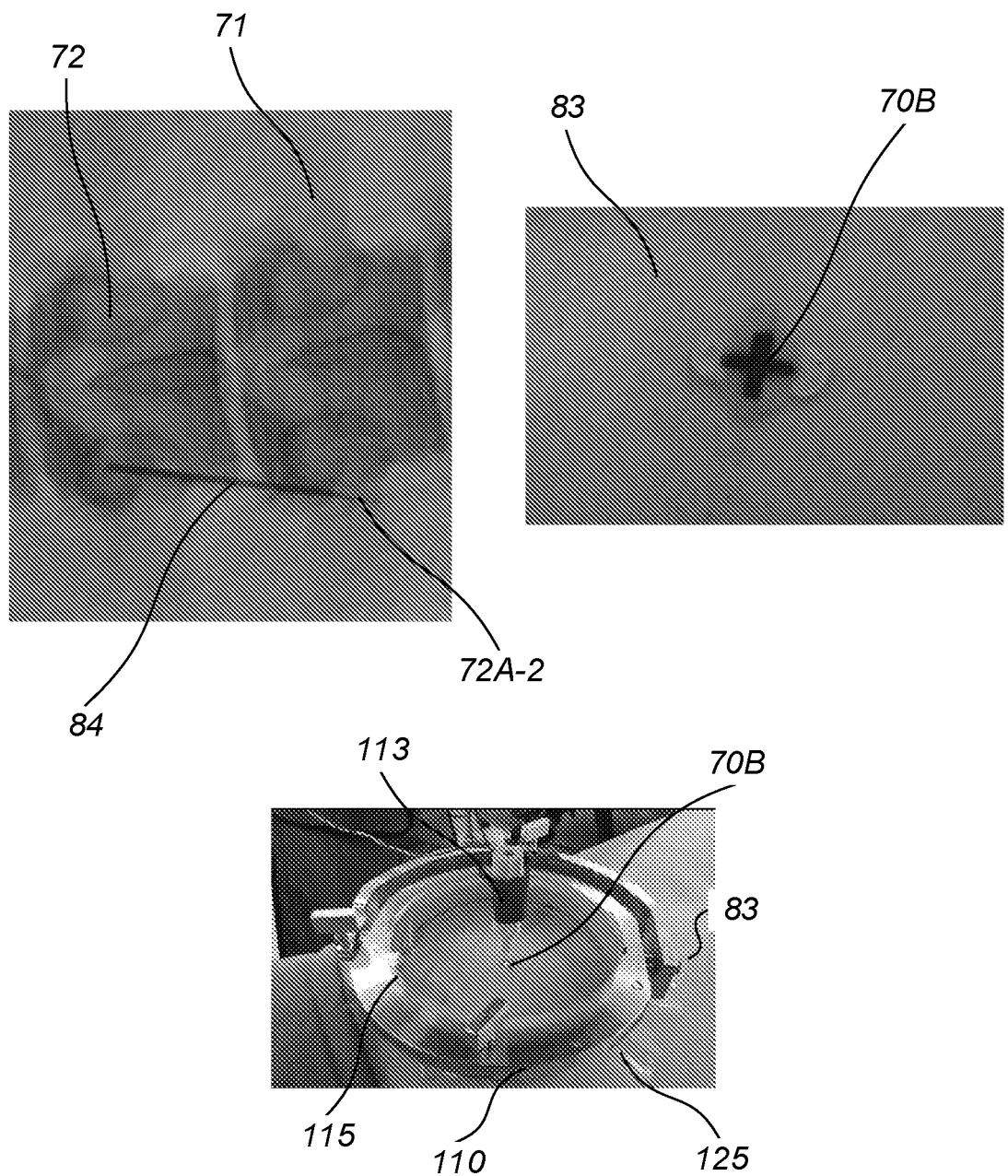

At step 520, X-Ray arm 87 (see, e.g., FIG. 2) is moved horizontally to place radio opaque marker 70A as seen in the X-Ray image to overlap treatment location 141 within the patient (see, e.g., 70A-2 in FIG. 6A). In certain embodiments, X-Ray intensifier 85 may be positioned in an angle to the treatment location 141, to overlap the radio opaque marker 70A onto treatment location 141. It is important to note that if an angle is set, it is done before step 520. This angle would be the desired angle of view, which is also the angle of FUS energy penetration to the patient body. At step 525, a radio opaque marker 70B is placed on patient's skin 83 in a specific location that the operating physician selects following verification of treatment location 141 using radio opaque marker 70A-2 during an X-ray image by temporarily placing at least one temporary marker 84 (e.g., tip of needle) on the patient skin 83 (see, e.g., FIG. 6B). In certain embodiments, marker 70B may be only/also visual marker. This marker has no significant acoustic absorption to avoid near field heating and damage to the patient skin by the FUS energy.

At step 530, coupling accessory 125 is placed on skin 83 of the patient above marker 70B, as in step 525. At step 535, cradle 110 with mockup 115 is placed on coupling accessory 125 (see e.g., FIG. 6B).

Figure 6C:
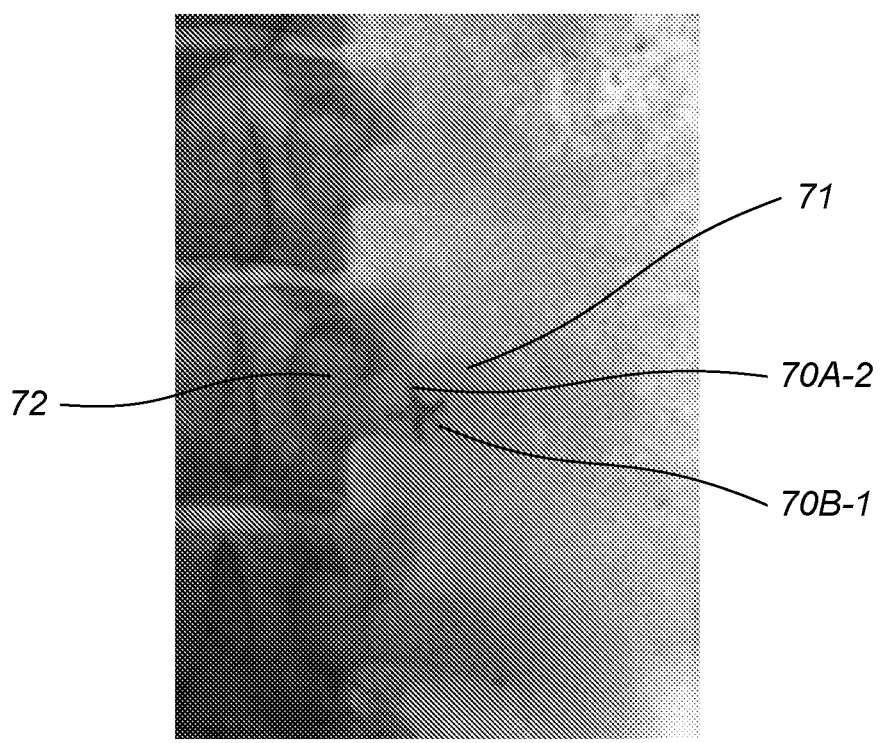

At step 540, at least one optical marker holder 113 on mockup 115 is turned on and cradle 110 is aligned using articulated arm 111 of apparatus 100 and pointing by co-linear lasers to radio opaque marker 70B on patient's skin 83 and radio opaque marker 70A on intensifier 85. At step 545, an X-Ray image is taken to verify the alignment of cradle 110 and mockup 115 to the normal of the center of the X-ray imaging system field of view along axis 112. At step 550, the verification of the alignment is performed. If radio opaque markers 70A-2, 70B-1 on the X-Ray image from step 545 are overlapped, it means that cradle 110 and mockup 115 are aligned with the normal of the center of the X-ray imaging system field of view along axis 112 (see, e.g., FIG. 6C). If radio opaque markers 70A-2, 70B-1 are not overlapped on the X-Ray image from step 545, the step 535 should be performed again. In certain embodiments, the alignment of cradle 110 and mockup 115 with the normal of the center of the X-ray imaging system field of view may be verified also using at least two x-ray aiming markers 133, 134 positioned on vertical axis of at least one optical marker holder 113. Once cradle 110 and mockup 115 are aligned with the normal of the center of the X-ray imaging system field of view along axis 112, x-ray aiming markers 133, 134 will appear concentric in the X-ray image from step 545 (see, e.g., FIG. 7A). If x-ray aiming markers 133, 134 are not seem concentric in the X-Ray image from step 545 (see, e.g., FIG. 7B), step 535 should be repeated. A certain range of position and angular error of aiming apparatus 130 may be permitted. An indication of the permitted error can be presented to the operating physician by the shape and/or size of x-ray aiming markers 133, 134, such as the gap between the aiming markers diameters, which must remain visible around inner x-ray aiming marker 133 to indicate alignment within the error limits. In certain embodiments the decision on the quality of alignment of the cradle and aiming apparatus, at this step, could be done based on optical markers alone without the need for X-Ray imaging.

In certain embodiments, the alignment of cradle 110 can be performed based on depth images produced by a depth camera located on cradle 110 or FUS transducer 120 facing intensifier 85. Cradle 110 may be aligned such that the flat face of intensifier 85 is parallel to cradle 110 according to the depth image analysis, and the shape of intensifier 85 is centered with the center of cradle 110 or FUS transducer 120, such that cradle 110, intensifier 85 and central axis 112 are collinear. In certain embodiments, the alignment of cradle 110 can be performed based on at least two distance sensors, such as but not limited to ultrasonic, RF, IR or laser sensors, located on cradle 110 or FUS transducer 120 facing intensifier 85. These sensors can measure the distance from intensifier 85 and indicate the alignment needed in order to bring cradle 110 to a parallel alignment relative to intensifier 85 face. Complimentary to the distance sensors, a camera located on cradle 110 or FUS transducer 120 facing intensifier 85 will produce an image of intensifier 85 round shape to indicate the position of cradle 110, relative to the intensifier 85, and the direction to move cradle 110 in order to co-align central axis 112, intensifier 85 and cradle 110. In certain embodiments, alignment of cradle 110 can be performed based on at least two dual axis tilt-meters or angulation sensors, located on cradle 110 or FUS transducer 120 and on intensifier 85. These sensors can measure the angle of cradle 110 or FUS transducer 120 and of intensifier 85 and indicate the alignment needed in order to bring cradle 110 to a parallel alignment relative to intensifier 85 face. This could be done based on absolute angle measurements or following calibration done at a baseline parallel orientation. Complementary to the angle sensors, a camera located on cradle 110 or FUS transducer 120 facing intensifier 85 will produce an image of intensifier 85 round shape to indicate the position of cradle 110, relative to intensifier 85, and the direction to move cradle 110 in order to co-align the central axis of intensifier 85 and cradle 110. The tilt-meters or angulation sensors can be wired or wireless and use any existing technology to measure the required angle.

At step 555, C-Arm 87 of the X-Ray imaging system is tilted laterally, preferably to an angle perpendicular to cradle axis 112 to verify the depth of treatment location 141, using the FUS beam path 140 recognized by the software module of workstation 180 (see, e.g., FIG. 3B). The tilting of C-Arm 87 should be performed preferably on a single axis. When using other types of imaging for guidance, such as CT, Ultrasound and other, the location of the transducer focus could be extrapolated from the image. Once the treatment depth is verified, within the applicable focus range, C-Arm 87 should be moved back to its previous vertical position. C-Arm 87 should be re-positioned in accordance with the angle of mockup 115, pointing optical markers holder 113 on radio opaque markers 70A and 70B. In certain embodiments, an X-Ray image may be taken again to verify the alignment.

At step 560, mockup 115 is removed from cradle 110 and transducer 120 is inserted into cradle 110. At step 565, an x-ray aim 150, is placed inside FUS transducer 120. At step 570, an X-ray image is taken to verify that cradle 110 and FUS transducer 120 are aligned with the normal of the center of the X-ray imaging system field of view along axis 112, as in step 550 using x-ray aim 150. At step 575, FUS acoustic energy beam 140 is deployed and the ablation of target position 141 is performed. In certain embodiments, the FUS acoustic energy could be first deployed at a low level to verify targeting, per patient, feedback before deploying an ablation level energy pulse.

Figure 8A:
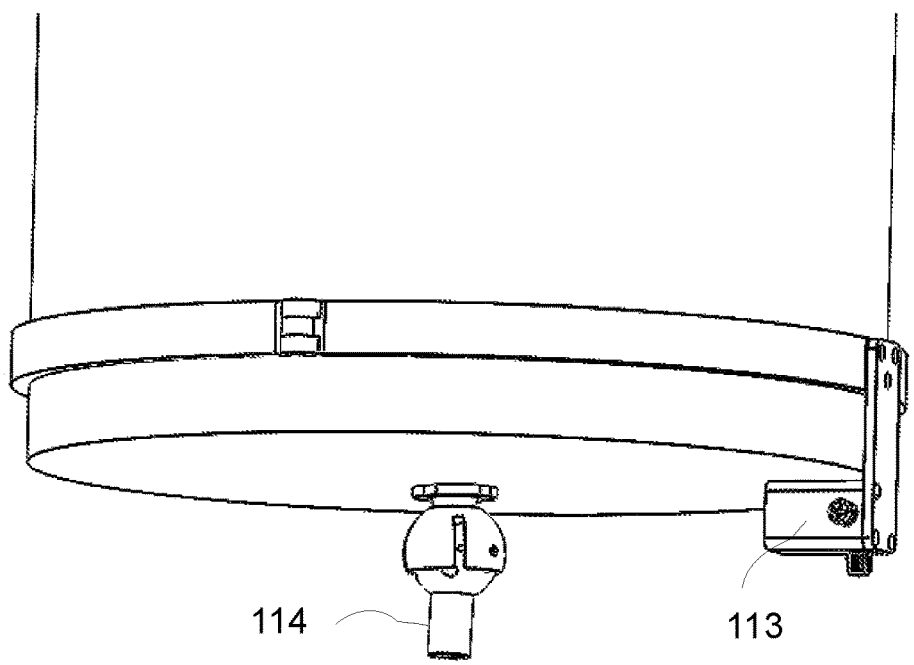
FIGS. 8A-8B are high level schematic illustrations and images of optical markers of different design used in the X-Ray guided device according to some embodiments of the invention
Figure 8B:
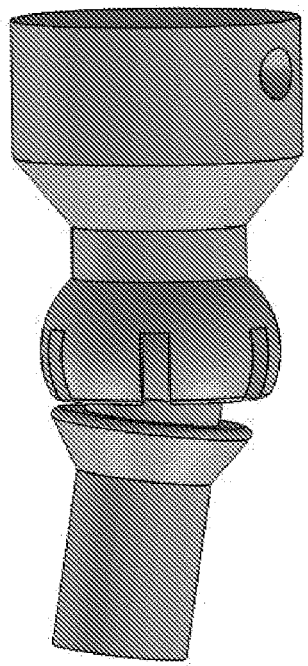

FIG. 8A-8B are high level schematic illustrations of optical marker holder being located in a different location, according to some embodiments of the invention. In these embodiments of the invention, since the laser beam originating from the optical marker 113 or mirror 114 is aligned with the central axis line of the C Arm 112, and the radio opaque marker in the center of the intensifier plate is adjusted to coincide with the treatment target on the X-ray image, the use of a mockup 115 is not required. Instead, an X-ray/optical aim attached directly to the FUS transducer can be used.

The optical marker holder 113 (FIG. 8A) or a mirror 114 (FIG. 8B) may be attached to the center of C Arm (X-Ray) intensifier plate 85. The optical marker holder 113 or mirror 114 may be designed to allow angular alignment relative to the intensifier plate, either manually and/or automatically, and to be aligned with the central axis 112 of the C Arm (FIG. 2) by projecting a laser beam to the center of the C Arm source 86 (FIG. 2). The optical marker 113 or mirror 114 may be attached to or consist of a radio opaque marker that is visible on X-ray image. The optical marker 113 or mirror 114 may be placed on the center of the radio opaque marker as applicable. In FIG. 8A the mirror 114 has an angular alignment capability while the optical marker 113 can be adjusted to aim the center of this mirror.

Figure 9A:
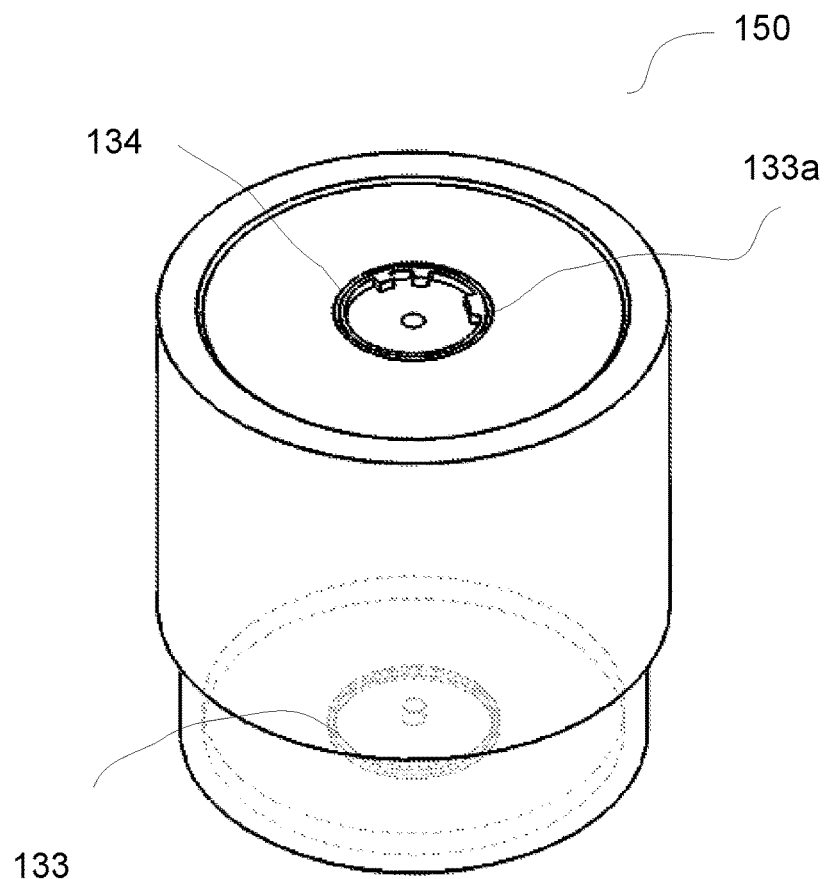
FIGS. 9A-9B are high level schematic illustrations of a modified x-ray aim of different design, used in the X-Ray guided apparatus according to some embodiments of the invention.
Figure 9B:
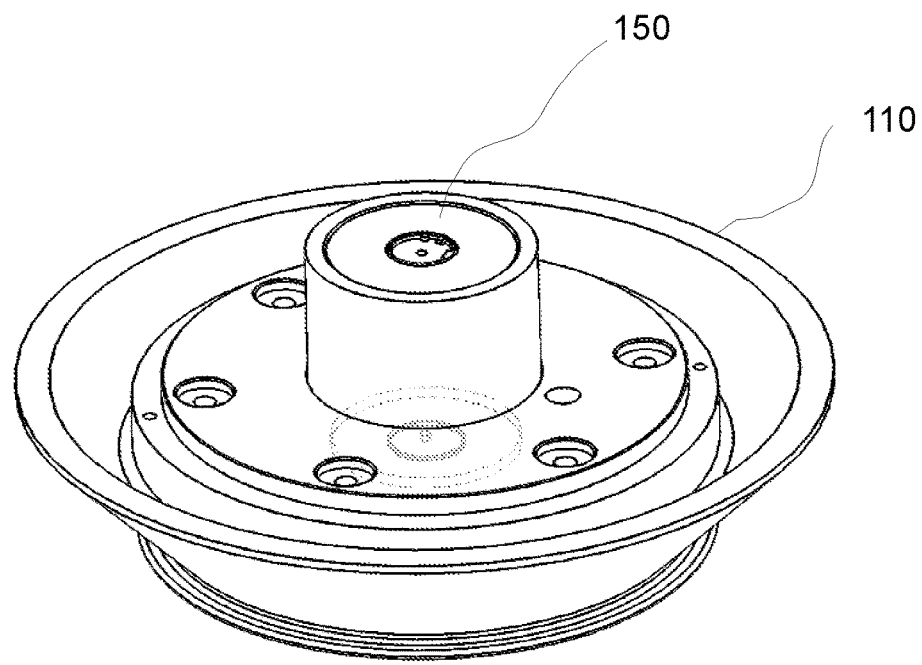

FIG. 9A-9B are a high level schematic illustrations of modified x-ray aim 150 affixed in FUS transducer 120, according to some embodiments of the invention. Modified x-ray aim 150 may be used as an optical aim and also an x-ray aim.

Figure 7A:
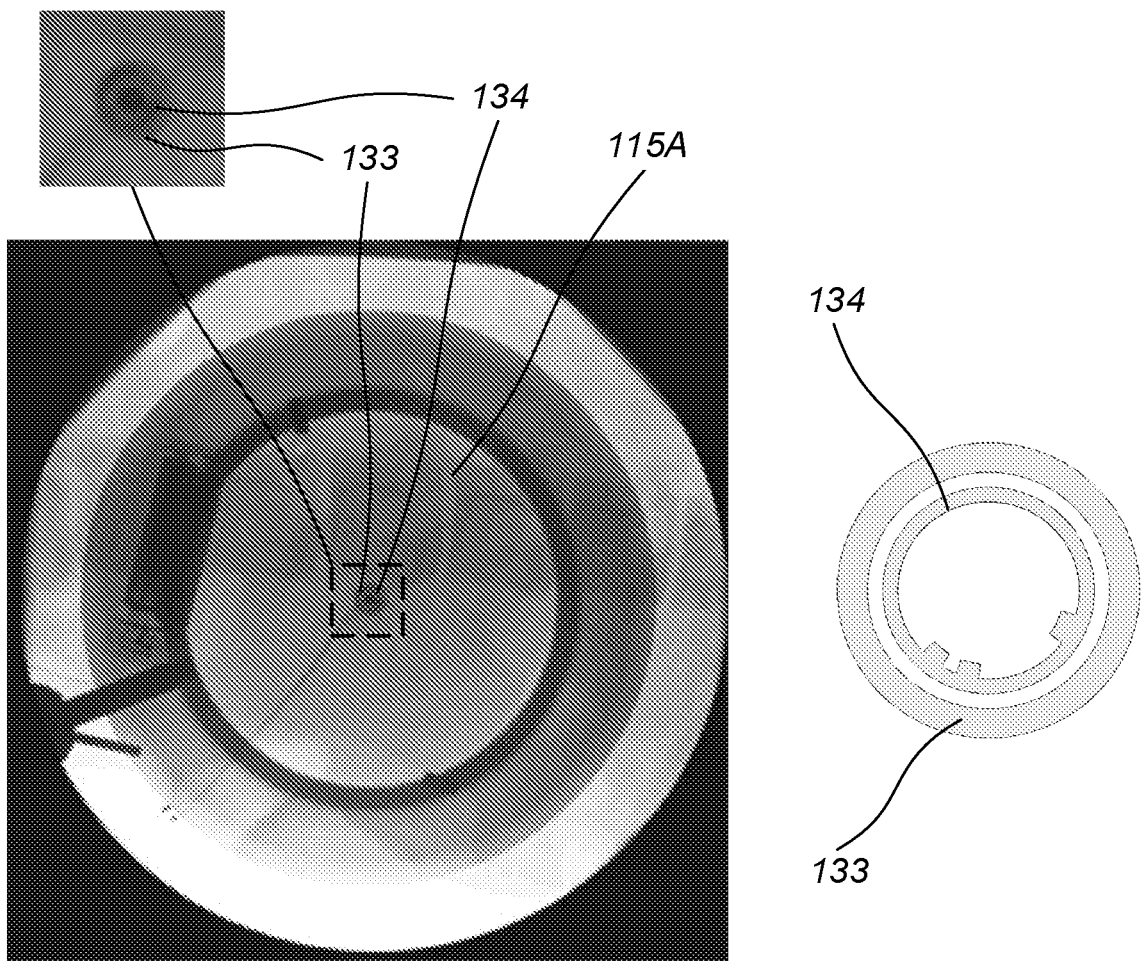
FIGS. 7A-7B is a high level schematic illustration of the aiming markers of the aiming apparatus.
Figure 7B:
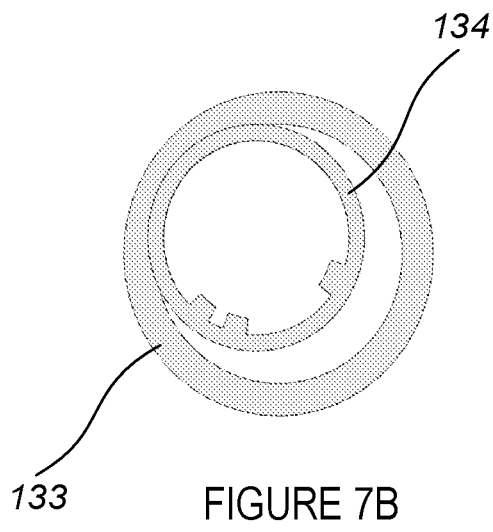
Figure 10:
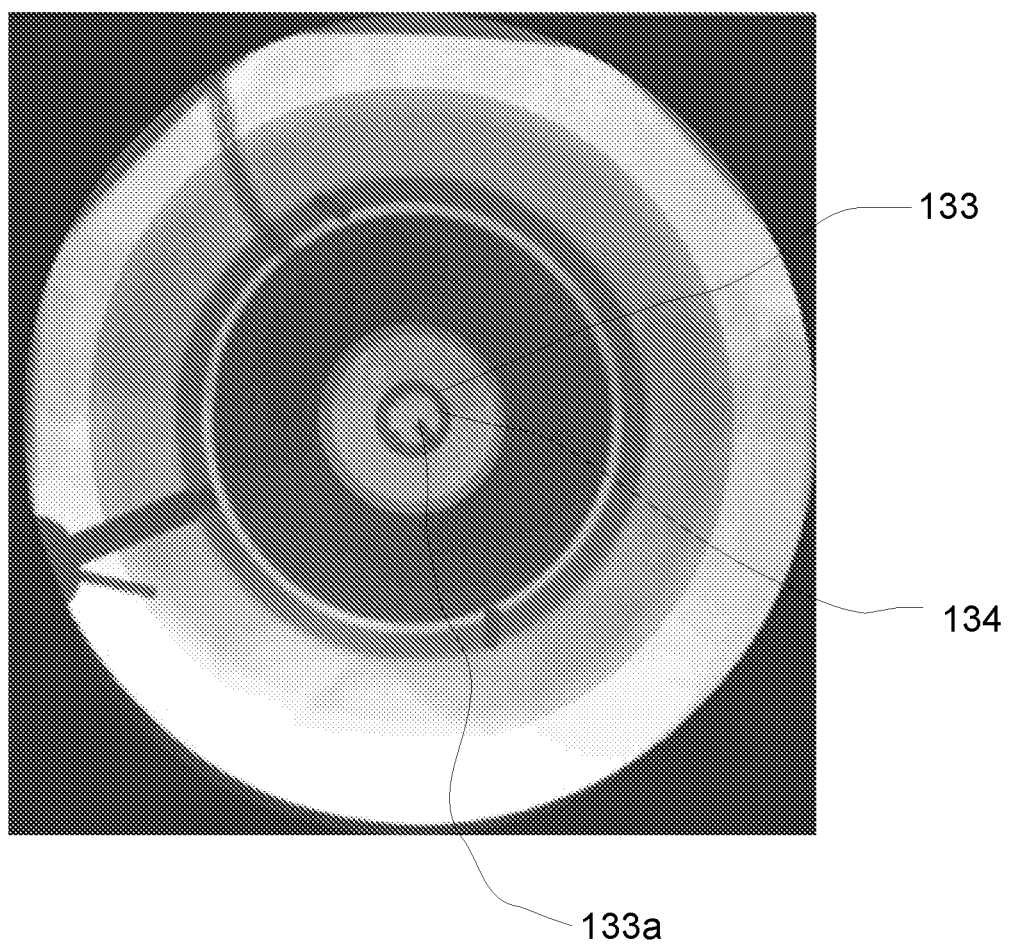
FIG. 10 is an X-Ray image of the modified x-ray aim at a suitable alignment.

Modified x-ray aim 150, which is placed in the socket or recess of FUS transducer 120 along central axis 112 of the FUS transducer, may contain two or more x-ray aiming markers, such as rings 133, 134, that are placed along the vertical axis of the FUS transducer. In order to align the FUS transducer to point to the target, the optical marker needs to appear at the center of the upper and lower rings 133, 134. In order to verify that the FUS transducer is aligned accurately to the C Arm central axis 112, the radio opaque rings 133,134 need to appear concentric on the X-ray image (FIG. 7A, FIG. 10). If the rings do not seem concentric in the image (FIG. 7B) or the physician identifies movement, the physician shall repeat the positioning procedure.

A certain range of position and angular error of modified x-ray aim 150 may be permitted. An indication of the permitted error can be presented to the physician by the shape and/or size of the x-ray aiming markers 133, 134, such as the gap between the ring diameters (FIG. 7A-7B), which must remain visible around the inner ring 133 to indicate alignment within the error limits.

Figure 11A:
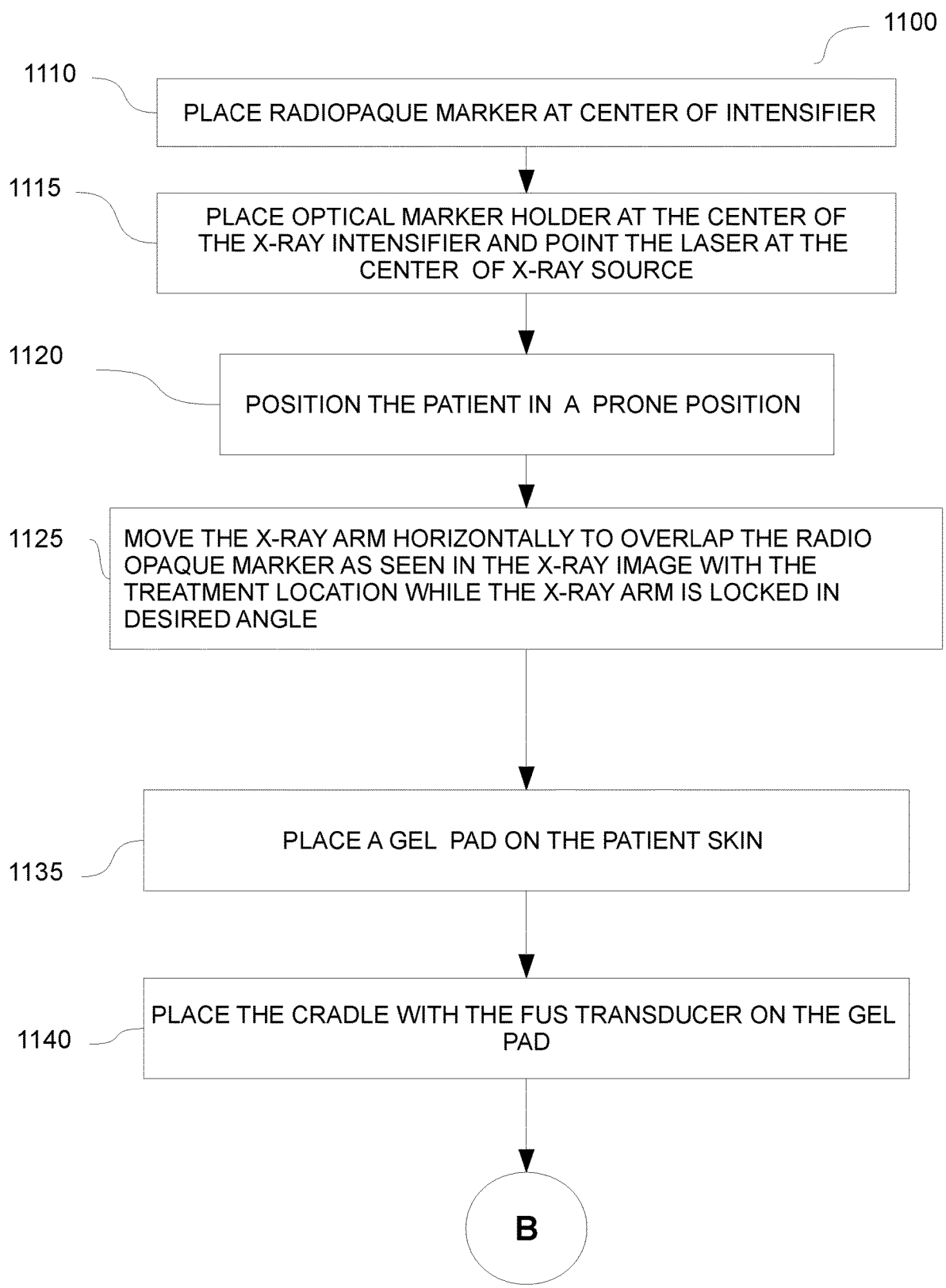
FIGS. 11A-11B is a high level flowchart illustrating another method, according to some embodiments of the invention.
Figure 11B:
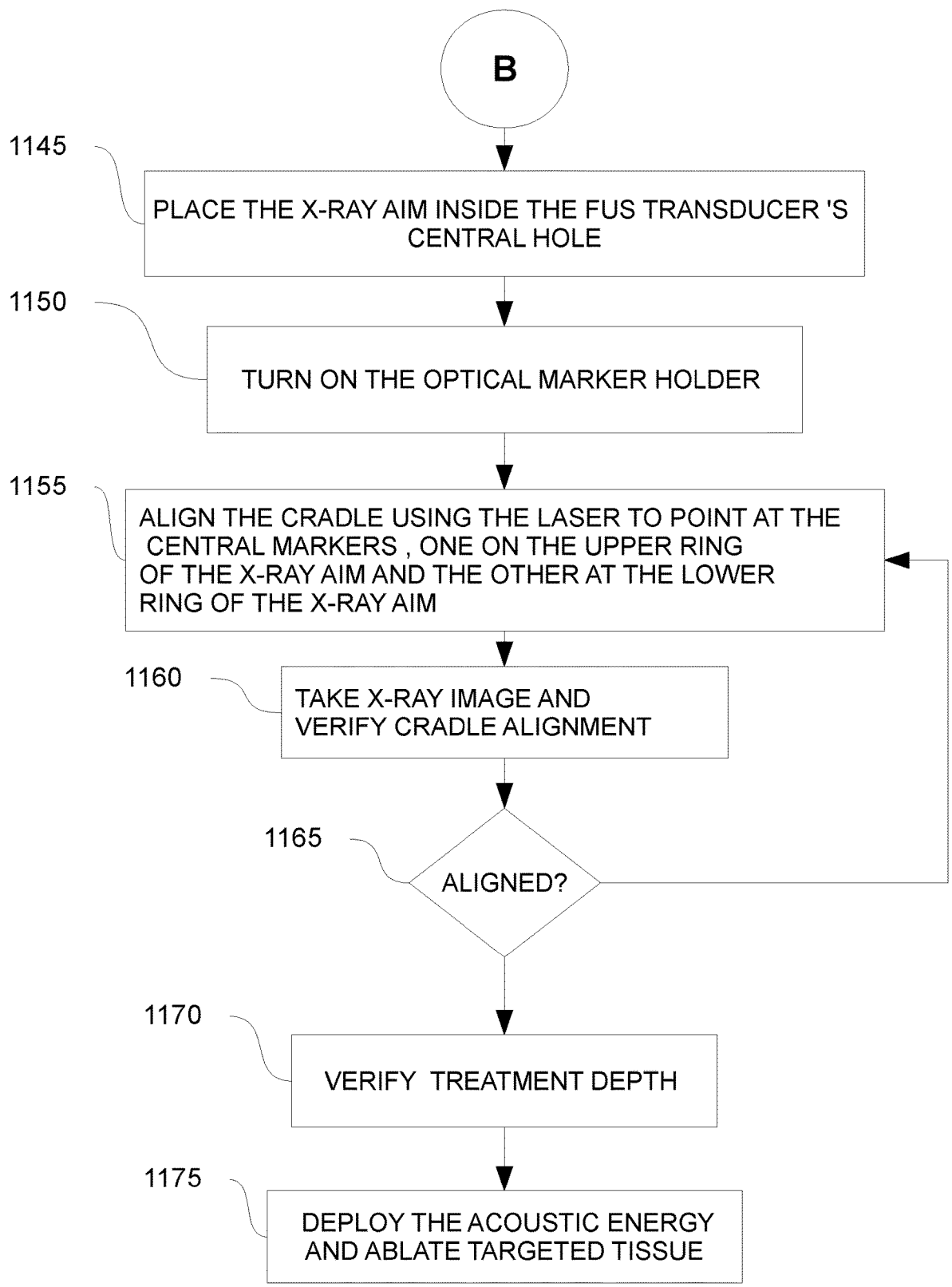

Reference is now made to FIGS. 11A-11B, which is a schematic flow diagram of a method 1100 for image guided focused ultrasound treatment to a patient, in some embodiments of this configuration.

At step 1110, a radio opaque marker may be placed at the center of the X-ray intensifier plate. An optical marker holder may then be placed at the center of the X-ray intensifier as per step 1115, and aimed at the X-ray source.

At step 1120, the patient is positioned in a prone position at a procedure platform 90. After the patient is positioned on the table, the relative height of the table and C-Arm is adjusted so that both the patient spine and the cradle can be seen within the X-Ray field of view. Once the height is set, it will remain lock throughout the procedure. This adjustment is done via lateral X-Ray image and manipulation of the table height and C-Arm height.

At step 1125, X-ray arm 87 is moved horizontally to place the radio opaque marker 70A as seen in the X-ray image to overlap the treatment location 141 within the patient (see, e.g., 70A-2 in FIG. 6A). In certain embodiments, X-Ray intensifier 85 may be positioned in an angle to the treatment location 141, to overlap the radio opaque marker 70A onto treatment location 141. It is important to note that, if an angle is set, it is done before step 520. This angle would be the desired angle of view, which is also the angle of FUS energy penetration to the patient body.

At step 1135, coupling accessory 125 is placed on skin 83. At step 1140, the cradle 110 with the FUS transducer 120 is placed on coupling accessory 125. At step 1145, the modified x-ray aim 150 is placed inside the central hole of the FUS transducer 120.

At step 1150, the at least one optical marker holder (FIGS. 8A-8B) on the X-ray intensifier 85 is turned on, and the alignment of the cradle is performed, using the laser to point at the central markers as per step 1155, one on the upper ring 133 of the modified x-ray aim 150 and the other at the lower ring 134 of the modified x-ray aim 150 (FIG. 9A). In case the aiming markers 133, 134 appear concentric in the X-ray image, the cradle is aligned (FIG. 6A). If aiming markers 133, 134 are not seemed concentric in the X-ray image, step 1155 should be repeated. A certain range of position and angular error of the modified x-ray aim may be permitted. An indication of the permitted error can be presented to the physician by the shape and/or size of the aiming markers 133, 134, such as the gap between the ring diameters (FIG. 7A-7B), which must remain visible around the inner ring 133 to indicate alignment within the error limits. In certain embodiments, the decision on the quality of alignment of the cradle and aiming apparatus could be done based on optical markers alone without the need for X-Ray imaging.

At step 1170, the treatment depth should be verified. The X-ray arm shall be tilted laterally, preferably at 90 degrees to the Cradle axis 112 to verify the depth of the treatment location, using the imaging workstation beam path and focal point overlay (FIG. 3B).

In case the treatment location depth is verified within the applicable focus range, the physician will deploy the acoustic energy, and ablate targeted tissue as per step 1175. In certain embodiments, the acoustic energy could be first deployed at a low level to verify targeting per patient feedback before deploying an ablation level energy pulse.

According to certain embodiments, the X-ray aim 150 and the aiming apparatus 130 shape may be designed in a manner that reduces the interference to the image quality. FIGS. 12A-12G are high level schematic illustrations of X-ray images of the FUS transducer 120 with various X-ray aims 150 (12A-12C), of which FIG. 12D-12G are high level schematic illustrations of X-ray images of aiming apparatus 130 at different designs, according to some embodiments of the invention. Image 12H shows as reference the transducer without any aim inserted into it.

Figure 12F:
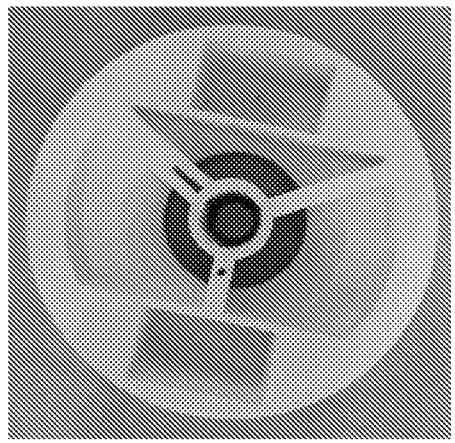

In all the X-ray aims presented, the design is optimized to minimize artifacts by eliminating non-aim related sharp interfaces between materials with different levels of radio opaqueness to make image as clear as possible. Similar effect, (to a bigger degree) can be seen in the design of the aiming apparatus, where FIG. 12D shows a design with many artifacts, and where FIG. 12E shows a clear design which is also optically transparent, as can be seen in FIGS. 12F-12G.

Figure 12G:
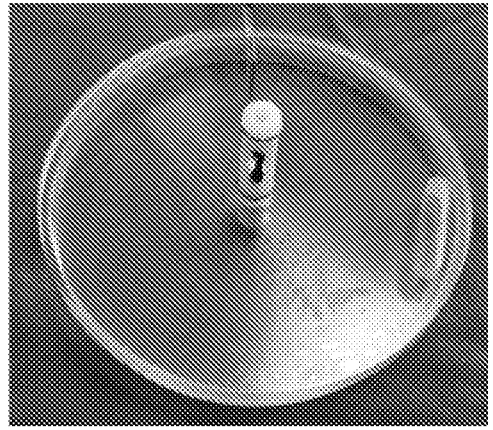
Figure 12H:
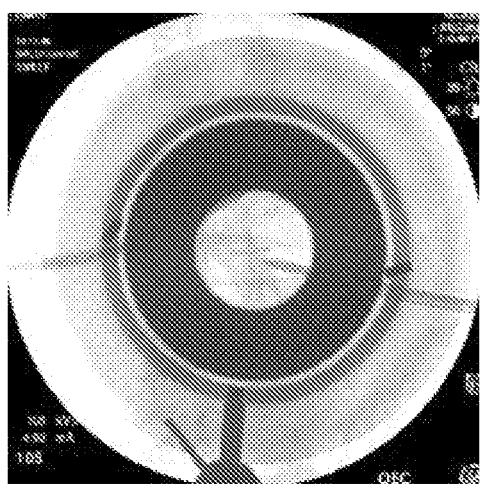

In addition, the bottom of the X-ray aim 150 has a thick disk-shaped plastic part which increases the overall radio opaqueness of the aim and allows a more balanced (in terms of gain and image saturation), imaging of the anatomy through the FUS transducer 120 opening as seen in FIGS. 12H-12G.

Figure 13A:
FIGS. 13A-13C are screen dumps of the baseline images (FIGS. 13A and 13B) and the result (FIG. 13C) of the device imaging workstation image processing of AP images with the transducer in place, according to some embodiments of the invention
Figure 13B:
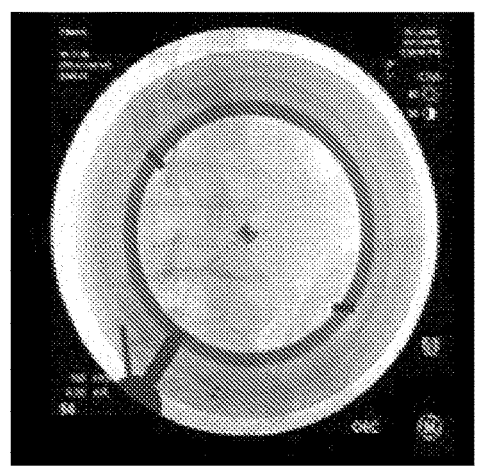
Figure 13C:
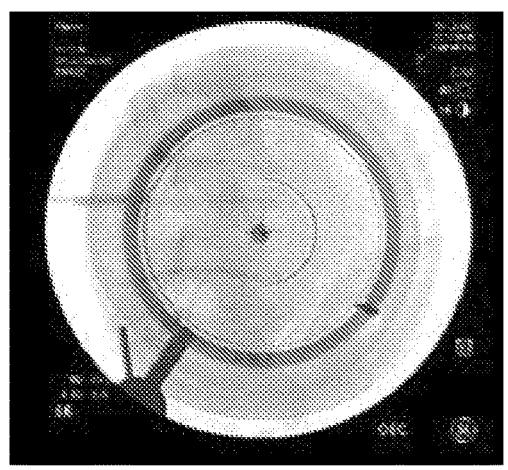

FIGS. 13A-13C are high level schematic illustrations of x-ray images of the treatment target with and without the FUS transducer in the cradle respectively, according to some embodiments of the invention. FIG. 13A illustrate the A-P images of the FUS transducer as shown on the device workstation during the procedure.

After the positioning process is over and the cradle is aligned with central axis 112 and fixed, the workstation may identify the circular shape of the cradle in the image, save it and use the clear image of its inner area including the treatment target (FIG. 13B) to replace the dark area caused by the radiopacity of the transducer (FIG. 13A) using image processing, thereby avoiding obstruction of the patient anatomy. This produces a clear image of the treatment target with the transducer inside the cradle (FIG. 13C) when ready for sonication. The physician may then observe the image, which shows now a radiologically "transparent transducer", which provides the anatomical information that was blocked by the opaque transducer. The importance of such image is to assist the physician to identify and verify the treatment location and alert in case of potential patient movement. These features are essential for the enhancement of the device safety profile and efficacy outcome.

Figure 14A:
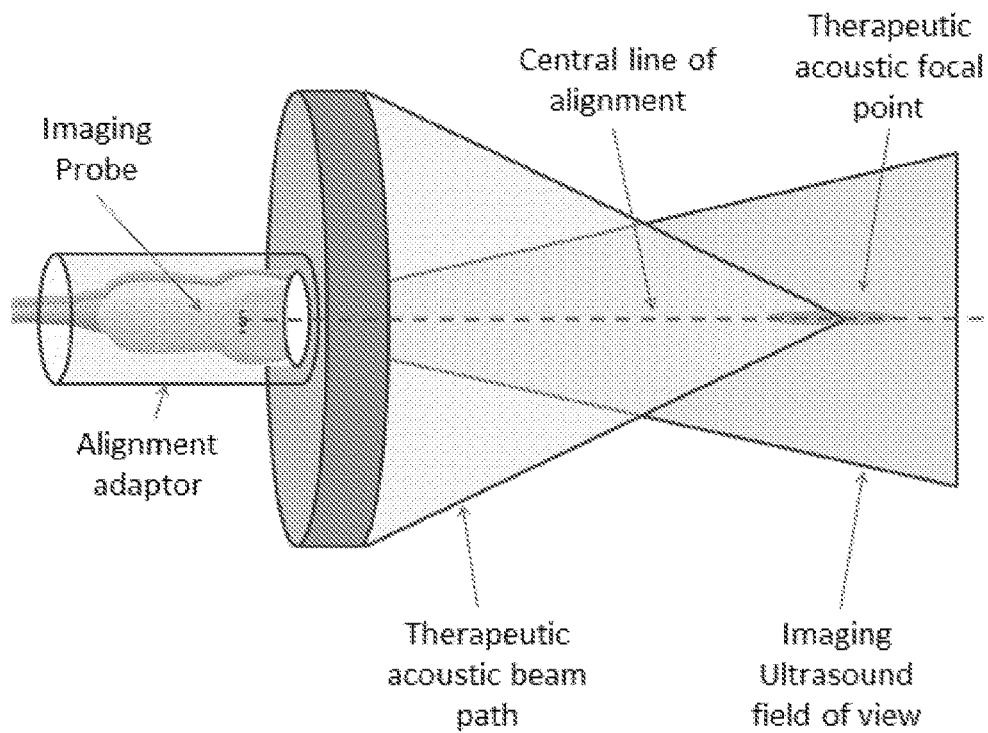
FIG. 14A-14B is a schematic diagram showing the alignment of the imaging and therapeutic ultrasound probes in the ultrasound guided device thereby positioning the therapeutic acoustic focal point in the center of the ultrasound image.

Another embodiment of this apparatus is using an ultrasound (US) imaging probe instead of using imaging of an X ray device, to view the treatment target and align the FUS transducer to it. FIG. 14A is a schematic illustration of the US imaging probe mounted in the center of the FUS transducer. An alignment adaptor is used to align the US imaging probe to conjoin with the transducer central axis.

Figure 14B:
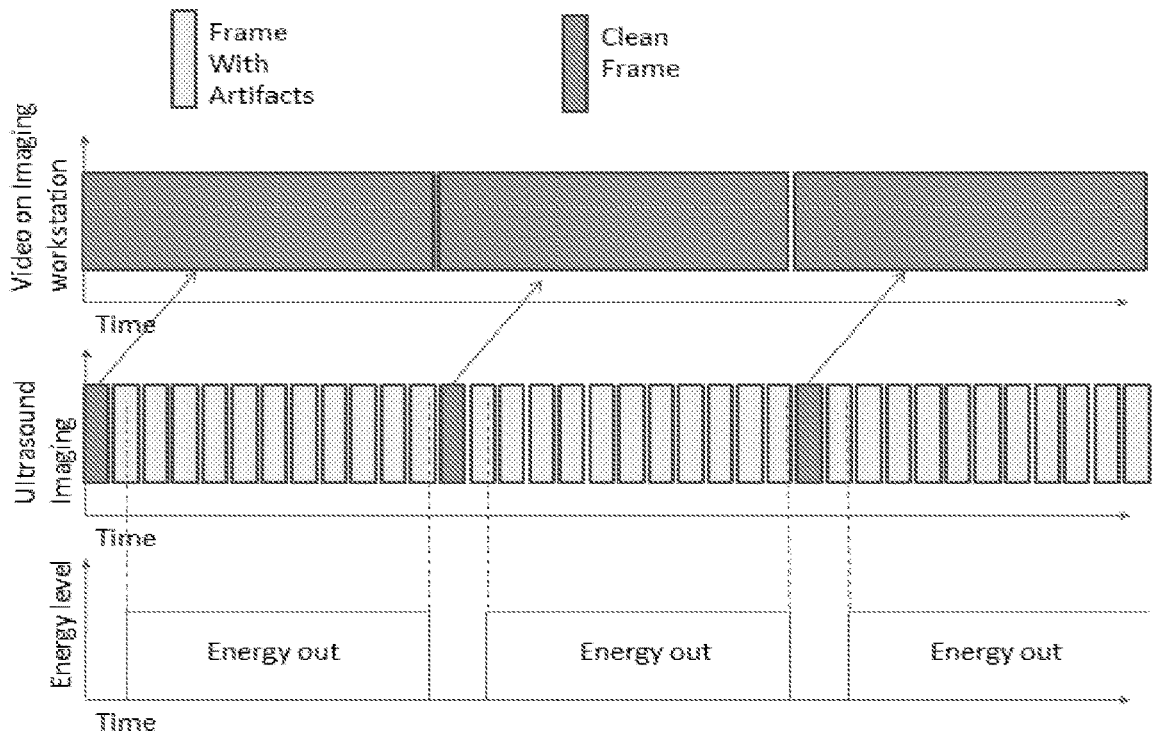

As the simultaneous operation of the imaging probe and transducer US sonication significantly degrades the quality of the ultrasound images and even completely blocks the imaging capabilities, an alternated pulsed method is described in FIG. 14B. The FUS energy will be pulsed with short time cease periods in which an image without artifacts or degradation would be captured from the ultrasound imaging stream to be presented on the imaging workstation until replaced by the next non-distorted image, captured at the next energy cease time period. This way the refresh rate of the imaging would be lower but can still produce an image feedback during sonication. The non-distorted images can be identified using basic image processing techniques as the predicted level of image degradation is significant. Alternatively the pulse to create the therapeutic sound wave may be created in such a manner to minimize artifacts and degradation of ultrasound image. It is important to note that the uniqueness of the implementation above is that is allows any generic ultrasound imaging system with the required imaging characteristics for the clinical indication to be used, as is, without any need for modification or connection to a gate signal, as guidance for a Focused Ultrasound system.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to the diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. An apparatus for a focused ultrasound (FUS) treatment operable in association with an X-Ray imaging system having an X-Ray intensifier, the apparatus comprising:
   a cradle having a conical shape;
   an aiming apparatus affixable within the cradle or affixable to the X-Ray intensifier;
   a FUS transducer comprising annular elements and operable to produce different geometric focal lengths, the FUS transducer affixable within the cradle and configured to transmit a FUS therapeutic energy beam to a treatment location, wherein an intersection point of projections of boundaries of the conical shape of the cradle corresponds to a focal point of the FUS transducer such that the conical shape of the cradle is configured to be used as a marker to guide a focusing of the FUS therapeutic energy beam to the treatment location;
   a controller coupled to the FUS transducer and configured to control the FUS therapeutic energy beam being transmitted by the FUS transducer; and
   an imaging workstation comprising a processing module, the processing module is configured to detect, over at least one lateral X-Ray image of the cradle, the projections of the boundaries of the conical shape of the cradle to thereby aid navigation of the FUS therapeutic energy beam to the treatment location.

2. The apparatus of claim 1, further comprising an articulated arm having a distal arm end affixed to the cradle, wherein the articulated arm is configured to enable at least one of:
   motion of the cradle in at least one of anterior-posterior (A-P), superior-inferior (S-I), and medial-lateral directions with respect to the procedure platform, and
   at least one of tilt, yaw, pitch and roll motions of the cradle with respect to the distal arm end, to thereby aim the FUS therapeutic energy beam onto the treatment location.

3. The apparatus of claim 1, wherein the imaging workstation comprises a screen, and wherein the processing module is configured to:
   receive at least one lateral X-Ray image of the cradle from the X-Ray imaging system;
   display, on the screen, the at least one lateral X-Ray image;
   display, on the screen, over the at least one lateral X-Ray image, the projections of the boundaries of the conic shape of the cradle.

4. The apparatus of claim 1, wherein the imaging workstation comprises a screen, and wherein the processing module is configured to:
   detect, in at least one X-Ray image, an area presenting the treatment location surrounded by the cradle,
   save a clear image of the area thereof,
   detect and replace, in at least one additional X-Ray-image, a dark area surrounded by the cradle with the clear image of the area thereof to thereby generate at least one updated X-Ray image, and
   display, on the screen, the at least one updated X-Ray image.

5. The apparatus of claim 1, wherein the aiming apparatus comprises: a mock-up removably affixable within the cradle, and at least one optical marker holder affixed to the mock-up.

6. The apparatus of claim 5, wherein the aiming apparatus comprises at least two ring x-ray markers, wherein each ring x-ray marker of the at least two ring x-ray markers is affixed to the at least one optical marker holder at a predetermined position along the at least one optical marker holder and has-different size as compared to other ring x-ray markers of the at least two ring x-ray markers.

7. The apparatus of claim 6, further comprising at least one radio opaque marker configured to be placed on the X-ray intensifier, and at least one of a visual marker and a radio-opaque marker configured to be placed on a skin of a patient above the treatment location.

8. The apparatus of claim 1, wherein the aiming apparatus comprises a depth camera, at least two distance sensors, and at least two angular sensors, configured to be located on at least one of: the cradle, the FUS transducer, the X-Ray intensifier and any combination thereof.

9. The apparatus of claim 1, wherein the aiming apparatus is affixable within the recess of the FUS transducer such that a central longitudinal axis of the aiming apparatus coincides with a central longitudinal axis of the FUS transducer.

10. The apparatus of claim 1, wherein the aiming apparatus comprises at least one of:
    an optical marker holder removably attachable to the X-Ray intensifier, or
    a mirror removably attachable to the X-Ray intensifier and an optical marker holder removably attachable to an edge of the X-Ray intensifier.

11. The apparatus of claim 1, further comprising a coupling accessory to acoustically couple the FUS transducer with a skin of a patient.

12. The apparatus of claim 11, wherein the coupling accessory is at least one of a balloon filled with an acoustic fluid or a gel pad.

13. The apparatus of claim 1, further comprising an imaging ultrasound (US) transducer removably affixable within a recces in the FUS transducer, the imaging US transducer is configured to generate US images of treatment location to thereby aid in navigation of the FUS therapeutic energy beam to the treatment location.

* * * * *